(12) United States Patent
Wheeler et al.

(10) Patent No.: US 11,660,021 B2
(45) Date of Patent: May 30, 2023

(54) DEVICES, METHODS, AND SYSTEMS FOR COLLECTION OF VOLATILE ORGANIC COMPOUNDS

(71) Applicant: DIAGNOSE EARLY, INC., Newark, CA (US)

(72) Inventors: Chris Wheeler, Atherton, CA (US); Chris Todd, Campbell, CA (US); Jeffrey A. Schuster, Alameda, CA (US); Karl-Magnus Larsson, East Palo Alto, CA (US)

(73) Assignee: Diagnose Early, Inc., Newark, CA (US)

( * ) Notice: Subject to any disclaimer, the term of this patent is extended or adjusted under 35 U.S.C. 154(b) by 518 days.

(21) Appl. No.: 16/714,298

(22) Filed: Dec. 13, 2019

(65) Prior Publication Data

US 2020/0187828 A1    Jun. 18, 2020

Related U.S. Application Data

(60) Provisional application No. 62/847,181, filed on May 13, 2019, provisional application No. 62/779,256, filed on Dec. 13, 2018.

(51) Int. Cl.
*A61B 5/097*  (2006.01)
*A61B 5/08*   (2006.01)
*G01N 33/00*  (2006.01)

(52) U.S. Cl.
CPC ............. *A61B 5/097* (2013.01); *A61B 5/082* (2013.01); *G01N 33/0011* (2013.01);
(Continued)

(58) Field of Classification Search
CPC .......... A61B 2217/002; A61B 2560/04; A61B 5/082; A61B 5/087; A61B 5/097;
(Continued)

(56) References Cited

U.S. PATENT DOCUMENTS 5,465,728 A    11/1995  Phillips
6,594,016 B1   7/2003   Te Lintel Hekkert et al.
(Continued)

FOREIGN PATENT DOCUMENTS

FR    2963675 A1 *  2/2012  ............... G01N 1/22
JP    H8-510948 A    11/1996
(Continued)

OTHER PUBLICATIONS

Espacenet English Translation of FR 2963675. (Year: 2012).*
(Continued)

*Primary Examiner* — Christine T Mui
*Assistant Examiner* — Kathryn Elizabeth Limbaugh
(74) *Attorney, Agent, or Firm* — Bret E. Field; Bozicevic, Field & Francis LLP

(57) ABSTRACT

A system comprises a mouth piece to receive exhaled air; a breath chamber to receive exhaled air; a valve to direct exhaled air along a desired flow path, direct purge gas along a desired flow path, control the rate of flow of purge gas, control the rate of flow of exhaled air, block the flow of purge gas, and/or block the flow of exhaled air; a source of purge gas; a CO2 cartridge to remove CO2; a water cartridge to remove water; a breath cartridge to capture VOCs from exhaled air; a temperature control system to control the temperature of CO2 cartridge, a water cartridge, and/or a breath cartridge; a cryostat to contain and limit heat flow to a cryogenic liquid; a flow meter designed to measure the flow of exhaled air and/or purge gas; and a pressure transducer to measure a pressure, a flow rate, and/or a flow volume.

41 Claims, 10 Drawing Sheets

(52) U.S. Cl.
CPC ..... *G01N 33/0047* (2013.01); *G01N 33/0073* (2013.01); *A61B 2217/002* (2013.01); *A61B 2560/04* (2013.01)

(58) Field of Classification Search
CPC ............. A61B 5/4082; G01N 33/0011; G01N 33/0047; G01N 33/0073; G01N 33/497; G01N 33/57484; G01N 2033/4975; G01N 2800/12; C12Q 1/70
See application file for complete search history.

(56) References Cited

U.S. PATENT DOCUMENTS

| | | | |
|---|---|---|---|
| 11,075,068 | B2 | 7/2021 | Vidal-de-Miguel |
| 2001/0054324 | A1 | 12/2001 | Cole et al. |
| 2003/0109794 | A1 | 6/2003 | Phillips |
| 2009/0042309 | A1 | 2/2009 | Van Herpen |
| 2013/0125564 | A1 | 5/2013 | Booth |
| 2015/0335267 | A1* | 11/2015 | Cormier ............... A61B 5/0836 600/532 |
| 2017/0074857 | A1 | 3/2017 | Dennis et al. |
| 2017/0191910 | A1* | 7/2017 | Laskowski ........... A61B 5/7285 |

FOREIGN PATENT DOCUMENTS

| | | | |
|---|---|---|---|
| JP | H11-258255 A | 9/1999 | |
| JP | 2008-530577 A | 8/2008 | |
| WO | WO-9726827 A1 * | 7/1997 | ............. A61B 10/00 |

OTHER PUBLICATIONS

International Search Report and Written Opinion dated Mar. 3, 2020 in International Application No. PCT/US19/66143 filed Dec. 13, 2019 (16 pages).

Linus Pauling et al., "Quantitative Analysis of Urine Vapor and Breath by Gas-Liquid Partition Chromatography", (orthomolecular medicine/vitamins/controlled diet), Proc. Nat. Acad. Sci. USA, vol. 68, No. 10, pp. 2374-2376, Oct. 1971.

J. K. Mansoor et al., "Analysis of Volatile Compounds in Exhaled Breath Condensate in Patients with Severe Pulmonary Arterial Hypertension", PLOS | One, Published: Apr. 18, 2014, https://doi.org/10.1371/journal.pone.0095331.

Morad K. Nakhleh et al., "Diagnosis and Classification of 17 Diseases from 1404 Subjects via Pattern Analysis of Exhaled Molecules", ACS Nano, vol. 11, pp. 112-125, 2017.

Takashi Nagaoka et al., "Double Cold Trap Method to Determine the Concentrations of Volatile Organic Compounds in Human Expired Gas", Advanced Biomedical Engineering, vol. 4, pp. 112-118, 2015.

M. Alonso, J.M. Sanchez, "Abstract of Analytical challenges in breath analysis and its application to exposure monitoring", Trends in Analytical Chemistry, vol. 44, Mar. 2013, p. 78-89, https://doi.org/10.1016/j.trac.2012.11.011.

J. Liu et al., "Collection devices influence the constitutents of exhaled breath condensate", European Respiratory Journal, vol. 30, No. 4, pp. 807-808, Nov. 2007.

Arnold Wexler, "Vapor Pressure Formulation for Ice", Journal of Research of the National Bureau of Standards—A. Physics and Chemistry, vol. 81A, No. 1, Jan.-Feb. 1977.

Abstract of Baron and Willeke (B&W) Aerosol Measurement, 2nd Edition, J Wiley and Sons, 2001.

* cited by examiner ured heating to release the captured VOCs.
DEVICES, METHODS, AND SYSTEMS FOR COLLECTION OF VOLATILE ORGANIC COMPOUNDS

CROSS REFERENCE TO RELATED APPLICATION

This application claims priority to U.S. Provisional Application No. 62/779,256, filed Dec. 13, 2018, and U.S. Provisional Application No. 62/847,181, filed May 13, 2019, each of which is incorporated herein in its entirety.

TECHNICAL FIELD

The present disclosure relates to methods and devices for collection, storage, transport, assay, and analysis of volatile organic compounds from exhaled breath.

BACKGROUND

Volatile organic compounds, or "VOCs", are simple molecules comprised of carbon, hydrogen, and possibly oxygen, sulfur, and/or nitrogen. VOCs are present in exhaled breath at levels around 1 part per billion (PPB). It is believed that the levels of VOCs in exhaled breath can be used a biomarkers for certain disease states, including but not limited to cancer, Parkinson's disease, multiple sclerosis (MS) and others.

Linus Pauling et. al. (Proc. Nat. Acad. Sci. USA 68(10), 2374-2376 (1971)) captured exhaled VOCs (10-15 exhalations per sample), by trapping them in a coiled 5-foot by 0.20-inch ID stainless-steel tube cooled in an isopropyl alcohol dry ice bath at −78° C. The VOCs were then transferred to a gas chromatograph by uncontrolled heating with a heat gun.

Mansoor et. al. (Analysis of Volatile Compounds in Exhaled Breath Condensate in Patients with Severe Pulmonary Arterial Hypertension. PLoS ONE, 9(4): e95331, 2014) collected exhaled VOCs using the Jaeger EcoScreen (Viasys Healthcare, Conshohocken, Pa.) apparatus. Analysis by Gas Chromatography/Mass Spectrometry (GC-MS) suggested that exhaled VOCs may be useful in the diagnosis of pulmonary hypertension.

Nakhleh et. al. (Diagnosis and Classification of 17 Diseases from 1404 Subjects via Pattern Analysis of Exhaled Molecules, ACS Nano 11, 112-125, 2017) used an artificially intelligent nanoarray that is based on chemiresistive layers of molecularly modified gold nanoparticles and random network of single-wall carbon nanotubes, combined with GC-MS to show that relative levels of 13 exhaled VOCs were correlated with and possibly predictive of 17 distinct disease states.

Nagaoka et. al. (Double Cold Trap Method to Determine the Concentrations of Volatile Organic Compounds in Human Expired Gas, Advanced Biomedical Engineering 4: 112-118, 2015) used a −80° C. cold trap comprised of a tube filled with steel glass wool to measured exhaled VOCs. The captured VOCs were released in a gas chromatograph by heating the tube to 80° C.

Alonso et. al. (Analytical challenges in breath analysis and its application to exposure monitoring, TrAC Trends in Analytical Chemistry 44, 78-89, 2013) describe several methods of collecting breath samples for storage and transport. These include methods of real time analysis, which " . . . require complex, non-portable and expensive instrumentation, which limits their applicability for on-site determinations in exposure analysis". Also described methods of collecting exhaled breath for transport to an analytical site. These including cannisters, glass bulbs, and polymer sampling bags. These methods all suffer from varying rates of VOC loss because of the large surface area which is presented to the sample, background contamination, the potential for breakage, significant cleaning requirements, and the requirement for concentration of the VOCs at the analytical site. The authors also describe collection of VOC samples onto a sorbent material. However, sorbent materials do not collect all VOCs and have reduced collection efficiencies for the VOCs they do collect. These reduced collection efficiencies can vary, for example with the amount of sorbent material, the properties of the sorbent material, and the temperature at which the collection is conducted.

Liu et al (Collection devices influence the constituents of exhaled breath condensate, European Respiratory Journal 30: 807-808; 2007) compared 4 different VOC collection devices and concluded that "collection devices significantly affect exhaled breath condensate biomarker levels and absolute values from different devices are not directly comparable" suggesting variable an inefficient collection from the tested devices.

SUMMARY

It is a problem with the collection systems and methods in the prior art that collection occurs at approximately −80° C. or higher, which leads to inefficient and variable collection because it is above the condensation temperature of exhaled VOCs.

It is a problem with collection systems in the prior art that collection efficiencies of some VOCs are essentially zero, leading to the loss of information that may be valuable in the diagnosis of various disease states.

It is a problem with collection systems in the prior art that they require heating to release the VOCs, which release may be inefficient and variable.

There is a need for a system that captures one or more VOCs from exhaled breath with very high efficiency and reproducibility while maintaining lossless storage of the VOCs during transport, storage, and assay.

There is a need for such a VOC capture system also to specifically remove water prior to assay in order generate a sample with a very low water content to allow an accurate and sensitive quantitative GC-MS assay.

It is an object of an embodiment of the disclosed methods, systems, and apparatus to collect and quantify exhaled VOC's in human and animal breath.

It is an object of an embodiment of the disclosed methods, systems, and apparatus to assay the collected VOCs to determine absolute and/or relative levels of various VOCs.

It is an object of an embodiment of the disclosed methods, systems, and apparatus to analyze assayed VOC levels to identify correlations with various disease states.

It is an object of an embodiment of the disclosed methods, systems, and apparatus to use the identified correlations to diagnose various disease states.

It is an object of an embodiment of the disclosed methods, systems, and apparatus to use the identified correlations to diagnose disease states selected from the list including but limited to cancer, Parkinson's disease, MS.

It is an advantage of an embodiment of the disclosed methods, systems, and apparatus that no absorbing material is used in the collection of the VOCs so that control of the properties and amount of sorbent material is not required, and no or less heating of the collection apparatus is required to release the captured VOCs.

It is an advantage of an embodiment of the disclosed methods, systems, and apparatus that exhaled VOCs are captured by adsorption onto the inside surface of channels, without the addition of surface area maximizing components such as stainless steel, to minimize the amount of each VOC bound to the surface when heated to room temperature or above.

It is a feature of an embodiment of the disclosed methods, systems, and apparatus that the collection of the exhaled VOCs is accomplished by cooling the collection apparatus.

It is an advantage of an embodiment of the disclosed methods, systems, and apparatus that liquid nitrogen (LN2) is used to cool the collection apparatus, as LN2 is readily available in a hospital or laboratory setting, and has a low boiling point.

It is an advantage of an embodiment of the disclosed methods, systems, and apparatus that essentially the entire exhaled amount of many different VOCs is collected, reducing the number of exhalations required to approximately one.

It is an advantage of an embodiment of the disclosed methods, systems, and apparatus that essentially the entire exhaled amount of many different VOCs is collected, removing dependence of the collection efficiency on such things as temperature, flow rate, residence time, tube length, and the like.

It is an advantage of an embodiment of the disclosed methods, systems, and apparatus that greater than about 50%, or greater than about 75%, or greater than about 90%, or greater than about 95%, or greater than about 99%, of 5 or more VOCs, or of 10 or more VOCs, or of 20 or more VOCs, or of 40 or more VOCs, or of 80 or more VOCs, or of 160 or more VOCs, is collected.

It is an advantage of an embodiment of the disclosed methods, systems, and apparatus that essentially the entire exhaled amount of many different VOCs is collected, rendering the collection efficiency unchanged relative to design changes over the product life cycle, allowing for direct comparison of data from various design iterations.

It is an advantage of an embodiment of the disclosed methods, systems, and apparatus that prior to collection of the VOCs, exhaled water is removed, improving performance of the assay system, e.g. GC-MS.

It is an advantage of an embodiment of the disclosed methods, systems, and apparatus that prior to collection of the VOCs, exhaled CO2 is removed, improving performance of the assay system, e.g. GC-MS.

It is a feature of an embodiment of the disclosed methods, systems, and apparatus that the captured VOCs are contained in the collection device for greater than 1 hour with very low loss of VOCs.

It is a feature of an embodiment of the disclosed methods, systems, and apparatus that the captured VOCs are contained in the collection device for greater than 1 day with very low loss of VOCs.

It is a feature of an embodiment of the disclosed methods, systems, and apparatus that the captured VOCs are contained in the collection device for greater than 1 week with very low loss of VOCs.

It is a feature of an embodiment of the disclosed methods, systems, and apparatus that the captured VOCs are contained in the collection device for greater than 1 month with very low loss of VOCs.

It is an advantage of an embodiment of the disclosed methods, systems, and apparatus that the VOCs can be injected into an assay system, e.g. GC-MS, from the collection apparatus automatically using commercially available handling system.

It is an advantage of an embodiment of the disclosed methods, systems, and apparatus that the VOCs can be injected into an assay system without heating above room temperature.

These and other objects, advantages, and features of the disclosed methods, systems, and apparatus will become apparent to those persons skilled in the art upon reading the details of the formulations and methodology as more fully described below.

In an embodiment, a system for diagnosing disease using exhaled breath, the system comprises elements selected from a mouth piece configured to seal to the lips of a subject and receive exhaled air from a subject; a breath chamber configured to receive exhaled air from the mouth piece; a valve configured to do one or more of: direct exhaled air along a desired flow path, direct purge gas along a desired flow path, control the rate of flow of purge gas, control the rate of flow of exhaled air, block the flow of purge gas, block the flow of exhaled air; a source of purge gas; a CO2 cartridge configured to removed CO2 from exhaled air; a water cartridge configured to remove water from exhaled air; a breath cartridge configured to capture one or more VOCs from exhaled air; a temperature control system configured to control the temperature of one or more of: a CO2 cartridge, a water cartridge, a breath cartridge; a cryostat configured to contain and limit heat flow to a cryogenic liquid; a flow meter designed to measure the flow of one or both of: exhaled air, purge gale; and a pressure transducer designed to measure one of: a pressure, a flow rate, a flow volume.

In some embodiments, the system may further comprise at least one of a mouthpiece, a water cartridge, a cooling system, and breath cartridge, wherein a subject exhales directly through the mouthpiece, water cartridge, and breath cartridge.

In some embodiments, the cooling system comprises LN2.

In some embodiments, the system further comprises at least one of a mouthpiece, a breath chamber, a breath cartridge, and a cooling system, wherein the cooling system comprises LN2.

In some embodiments, the subject exhales breath through the mouthpiece and breath chamber, and wherein the system further comprises valves to direct the exhaled breath through the breath cartridge when the subject is not exhaling.

In some embodiments, at least 50% of the breath cartridge is submerged in LN2.

In some embodiments, the breath cartridge comprises one or more channels.

In some embodiments, the breath chamber has a volume of less than or about 1 liter.

In some embodiments, the breath chamber has a volume of less than or about 0.5 liter.

In some embodiments, the breath chamber has a volume of less than or about 0.25 liter.

In some embodiments, the breath chamber has a volume of less than or about 0.1 liter.

In some embodiments, the breath chamber has a volume of less than or about 0.05 liter.

In some embodiments, the subject only exhales though the mouthpiece and breath chamber once.

In some embodiments, the system further comprises a source of purge gas, and further comprises two or more elements that allow for the simultaneous control of the gauge pressure in the breath cartridge and the flow through the breath cartridge, wherein the two or more elements are selected from the list consisting of a flow restriction; a pressure regulator; a flow controller; a needle valve.

In some embodiments, the gauge pressure in the breath cartridge is positive.

In some embodiments, the gauge pressure in the breath cartridge is greater than 1 kPa.

In some embodiments, the gauge pressure in the breath cartridge is greater than 2 kPa.

In some embodiments, the gauge pressure in the breath cartridge is greater than 4 kPa.

In some embodiments, the flow rate exiting the system is less than or about 0.5 liters per minute.

In some embodiments, the flow rate is less than or about 0.1 liters per minute.

In some embodiments, the flow rate is less than or about 0.05 liters per minute.

In some embodiments, given the molecular weight m of a VOC of interest, the combined length L of the one or more channels and the total flow rate at room temperature Q of the air flowing through the breath cartridge satisfy the relationship:

$$L/(m^{0.5}Q) > C$$

wherein L is in cm, m is in atomic mass units, Q is in liters per minute, and C=1.5.

In some embodiments, C=3.5.
In some embodiments, C=6.
In some embodiments, C=8.
In some embodiments, C=13.

In some embodiments, the system further comprises a water cartridge in series with the breath cartridge, wherein the breath cartridge has a combined total channel length of L' and it is run at a temperature T, wherein T, L', and Q satisfy the relationship $$L*T^{1.5}/Q*10000 > C$$

wherein Q is in liters per minute, T is in Kelvin, L is in cm, and C=5.

In some embodiments, C=11.
In some embodiments, C=16.
In some embodiments, C=21.

In some embodiments, when the subject exhales into the mouthpiece and breath chamber, the mouthpiece and breath chamber are fully integrated with the breath cartridge and LN2.

In some embodiments, when the subject exhales into the mouthpiece and breath chamber, the mouth piece and breath chamber are separated from the breath cartridge and LN2, and subsequently the breath chamber is integrated with the breath cartridge and LN2.

In some embodiments, the mouthpiece and breath chamber assembly have elements selected from an electrically activated valve; 2 or more electrically activated valves; an electronic pressure transducer; and a display.

In some embodiments, the mouthpiece and breath chamber assembly is all mechanical with no electrical parts.

In some embodiments, the breath chamber has check valves on its inlet and outlet.

In some embodiments, the check valves have a cracking pressure of greater than 0.25 kPa and less than 10 kPa.

In some embodiments, the end of the breath chamber that is not submerged in LN2 is held at a temperature of about −100° C. or higher.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
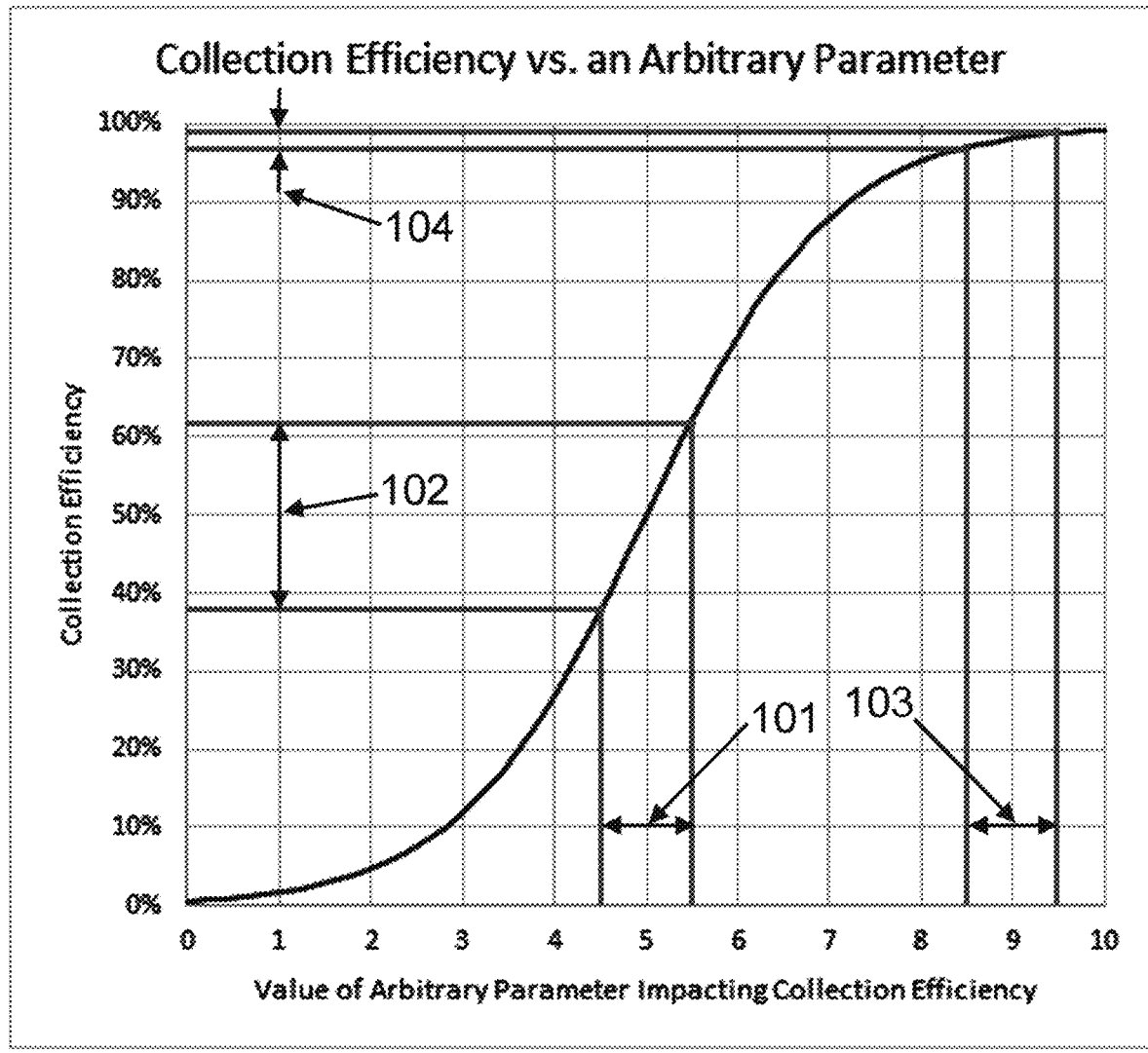
FIG. 1 is a diagram showing how efficient capture of VOCs leads directly to low variability, in accordance with an embodiment.

Before the present formulations and methods are described, it is to be understood that this invention is not limited to particular formulations and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It should be noted that the system described below has been developed and designed in the United States, and thus standard sizes in the imperial system of unit for tubing etc. have been used. It will be understood that readily-available metric equivalents may be used, and the current disclosure should be interpreted to include the standard metric equivalent both above and below the disclosed dimension.

It should be noted that much of the current disclosure describes tubing, channels, chambers, etc. in the shape of a right circular cylinder. This shape is generally preferred because it is manufacturable, readily available, and has the lowest exposed surface for a given cross sectional area. However, the disclosure is intended to cover other cross-sectional shapes, including but not limited to squares, rectangles, hexagons, and the like, or any arbitrary cross section. Standard methods, such as hydraulic diameter, can be used to calculate equivalent sizes of other shapes.

Definitions

Alveolar region: The region in the periphery of the lung where airways are densely lined with Alveoli.

Alveolus: A small (200-500) μm sac in the periphery of the lung where oxygen and other molecules in air such as VOCs are absorbed into the systemic circulation, and CO2 is removed from the systemic circulation.

Analysis: A detailed examination of something complex in order to understand its nature or to determine its essential features, for example analysis of measured VOC levels in exhaled breath to determine correlation with or to diagnose various disease states.

Anatomic dead space: The central region of the lung which is made up of relatively large conducting airways that are not alveolated. At the end of an inspiration, the anatomic dead space contains the last air inhaled, and that air does not equilibrate with the systemic circulation. Although there is some mixing, the first air exhaled at the beginning of an exhalation is largely air from the anatomic dead space, and is not equilibrated with, for example, the levels of VOCs in the systemic circulation.

Assay: Measurement of chemical constituents, especially amounts of VOCs in exhaled breath.

Ball Valve: A valve comprising a sphere with a through passage, which ball can be rotated to allow or disallow flow through the passage. Ball valves can be directional, directing flow from an inlet to one or more outlets, or directing flow from one or more inlets to an outlet. It will be understood that when ball valves are described in an example, any equivalent valve for blocking or directing flow can be substituted.

Breath Cartridge: An apparatus for collecting and concentrating VOCs from an exhaled air sample.

Breath Chamber: A holding vessel for capturing exhaled breath, especially prior to concentration of VOCs in a breath cartridge.

Check Valve: A valve that allows flow in only one direction. Preferred check valves have a low but greater than zero cracking pressure.

CO2 Cartridge: A device from removing CO2 from a sample of exhaled air.

Coefficient of Variation: The standard deviation of a series of measurements divided by the mean of the measurements. Usually quoted as a percentage.

Cold Finger: A rod with one end submerged in a cryogenic fluid, such as LN2, and the other end in thermal contact with an item (e.g. a water cartridge) to be cooled to a temperature above the temperature of the cryogenic fluid.

Condensation Temperature: The temperature at which a compound, preferably a VOC, will condense onto a surface if allowed sufficient time to diffuse to the surface. Condensation temperature depends both on the intrinsic properties of the compound and its partial pressure.

Cracking Pressure: The pressure required for a check valve to open and allow flow.

Cryostat: A container for a cryogenic fluid, such as LN2. Preferred cryostats have walls with reduced thermal conductivity, such as vacuum flasks and expanded polystyrene containers.

Cylinder: a rod of uniform cross section.

Dewar: Another name for a cryostat.

Diffusion Coefficient: A measure of the speed of diffusion of a molecule (such as H2O, CO2, or a VOC) or an ensemble of said molecules (i.e. a gas).

Diffusion: The process of a molecule (such as H2O, CO2, or a VOC) or an ensemble of said molecules (i.e. a gas) to propagate across a volume. Diffusion is in general driven by the thermal velocity of the molecules, and limited by collisions between the molecules.

End Tidal: Air from the end of an expiration. End Tidal breath is air wherein a large fraction has been in residence in the alveolar region of the lung, and thus is closer to being in equilibrium with the systemic circulation.

Flow Meter: An apparatus for measuring the flow rate of a gas, for example purge gas or exhaled air.

Gauge Pressure: Pressure above that of the surrounding air.

GC-MS: An analytical method that combines the features of gas-chromatography and mass spectrometry to identify different substances, preferably VOCs within a test sample which is preferably an exhaled breath sample.

Inert Gas: A gas that is relative non-reactive, including but not limited to helium, argon, xenon, krypton, and nitrogen.

LC-MS: An analytical method that combines the features of liquid-chromatography and mass spectrometry to identify different substances, preferably VOCs within a test sample which is preferably an exhaled breath sample.

LN2: Liquid nitrogen, a liquid of nitrogen (N2) molecules formed from cryogenically cooling nitrogen gas. When exposed to 1 atmosphere pressure, the boiling point of LN2 is −196° C.

Model Referenced Adaptive Control (MRAC): A control method used by a controller which adapts to conditions which vary in accordance to a model. An example would be a temperature control for a water trap, wherein the control parameters change as level of LN2 changes due to boil off.

Needle Valve: A valve with a screw thread tipped by a needle, which needle is directed toward a seat when the screw thread is advanced, thus reducing or stopping the flow of a gas. It will be understood that when needle valves are described in an example, any equivalent valve for reducing or directing flow can be substituted.

Organic Compound: A molecule which contains carbon. Some molecules, such as CO2 or CO, have traditionally not been considered to be organic compounds.

Pressure Transducer: A device, preferably solid state, for measuring pressure. With prior calibration, pressure transducers can be used to calculate flow rate of a gas, for example purge gas or exhaled air. By integrating the calculated flow rate over time, a gas volume can be calculated.

Proportional Integral Differential (PID) Servo Control: A control methodology which continuously calculates an error signal, for example the difference between a desired or "setpoint" temperature and a measured temperature, and applies a control signal, for example the current supplied to a heating resistor, proportional to the error signal, an integration over time of the error signal, and the time rate of change or "differential" of the error signal.

Proportional servo control: A control methodology which applies a control signal, for example the current supplied to a heating resistor, which control signal is proportional to an error signal, for example the difference between a desired setpoint such as a desired temperature and a measured setpoint such as a measured temperature.

Purge Gas: A gas that is flowed through a VOC collection system that is not a sample of exhaled air. Purge gas can be used to clear out VOCs, captured CO2 and H2O, and contaminants from previous measurements, force exhaled air samples through a collection system, and pressure a collection system, for example to eliminate the possibility of LN2 ingress.

Respiratory Bronchiole: A smaller branch of the bronchial airways in the respiratory tract that mark the start of the respiratory zone delivering air to the gas exchanging units of the alveoli.

Right circular cylinder: A cylinder wherein the cross section is a circle.

Saturated Air: Air containing the highest stable concentration of water vapor given the temperature of the air.

Sigmoid: An S shaped curve that, as function of some parameter, increases slowly at first, then the rate of increase rises to a maximum, followed by a decline in the rate of increase to essentially zero.

Snorkel: A section of tubing that allows a gas, for example air or an inert gas, to flow out of an apparatus submerged in a cryogenic fluid.

Sublimation: A process by which a compound, for example water, CO2, or a VOC, evaporates directly from a solid to a gas without going through a liquid phase.

Super Saturated Air: Air that has a higher than saturated water vapor content. Super saturation usually occurs by cooling saturated air, and can be maintained if there is no means to start condensation, such as a particle, surface, shear flow, or shock wave.

Surface to Volume Ratio: The ratio of a surface area to the volume of a shape, for example an air chamber.

Capture efficiency: The percentage of a compound, for example water, CO2, or a VOC, that is captured when flowed through a capture apparatus, for example a water cartridge, CO2 cartridge, or a breath cartridge. Also referred to as collection efficiency.

Thermo Electric Cooler (TEC): A solid-state device which transfers heat from one side of the device to the other, depending on the direction of applied electrical current.

Volatile Organic Compound (VOC): Organic compounds with high vapor pressure at room temperature.

Water Cartridge: A device for removing water vapor from a sample of exhaled air.

The current disclosure encompasses devices, systems, kits, and methods for collecting, detecting, and quantifying volatile organic compounds (VOCs) in breath exhaled by an animal, preferably a human. Although the disclosed methods, systems, and apparatus can be used to quantify a single VOC, preferably two or more VOCs are quantified, more preferably 5 or more, 7 or more, 10 or more, 15 or more, or 20 or more. In one embodiment, exhaled amounts of the one or more VOCs are individually quantified. In another embodiment, the relative amounts of more than one VOC are measured, and absolute amounts are not measured. In one embodiment, the system captures each VOC with a previously-quantified system capture efficiency (the percentage of the exhaled VOCs that are captured and presented for assay), and the results can be directly compared to other measurements that also have quantified system capture efficiencies. In another embodiment, the system capture efficiencies are not necessarily quantified, but the parameters relevant to the system capture efficiencies are controlled to yield a repeatable process wherein different measurements can be directly compared.

In some embodiments, large sample sizes are used to determine correlations with various disease states. Preferably sample sizes of more than or about 1000 samples, more than or about 10,000, more than or about 100,000, or more than or about 1,000,000 are used. Preferably techniques selected from a list including but not limited to artificial intelligence, regression, machine learning, neural networks, and the like are used to determine predictive correlations to various disease states. Preferably the disclosed methods, systems, and apparatus are then used to diagnose those disease states, or to indicate that more specific and predictive tests are required.

In a particularly preferred embodiment, the system capture efficiency for each VOC is sufficiently close to 100% that the system capture efficiency becomes relatively insensitive to parameter variation. This is shown schematically in FIG. 1. Capture efficiency may have a classic, "sigmoid" curve. As depicted, the x axis represents some parameter that is relevant to the capture efficiency, such as temperature, gas flow rate, length of capture medium, etc. The parameters that impact system capture efficiency for a preferred embodiment of the invention are discussed further below. When the capture efficiency is low, for example about 50% as shown in FIG. 1, the effect of the parameter may be large. Change 101 in the parameter of 1 in arbitrary units may lead to change 102 in capture efficiency of 24 percentage points. Since only about half of the VOC is captured, the percentage change in the amount of VOC captured (the "coefficient of variation") is about 24%/0.5=48%. This can be compared to the case when the capture efficiency is high, e.g., 98%. In this case, a change 103 of the same amount, 1, in the parameter leads to change 104 in the capture efficiency of only 1.83 percentage points, for a coefficient of variation of 1.87%. Thus, there is a non-obvious reproducibility benefit for a system with very high capture efficiency.

Preferably, system capture efficiencies for the VOCs of interest are greater than or about 50%, great than or about 75%, greater than or about 90%, greater than or about 95%, or greater than or about 99%.

Figure 2:
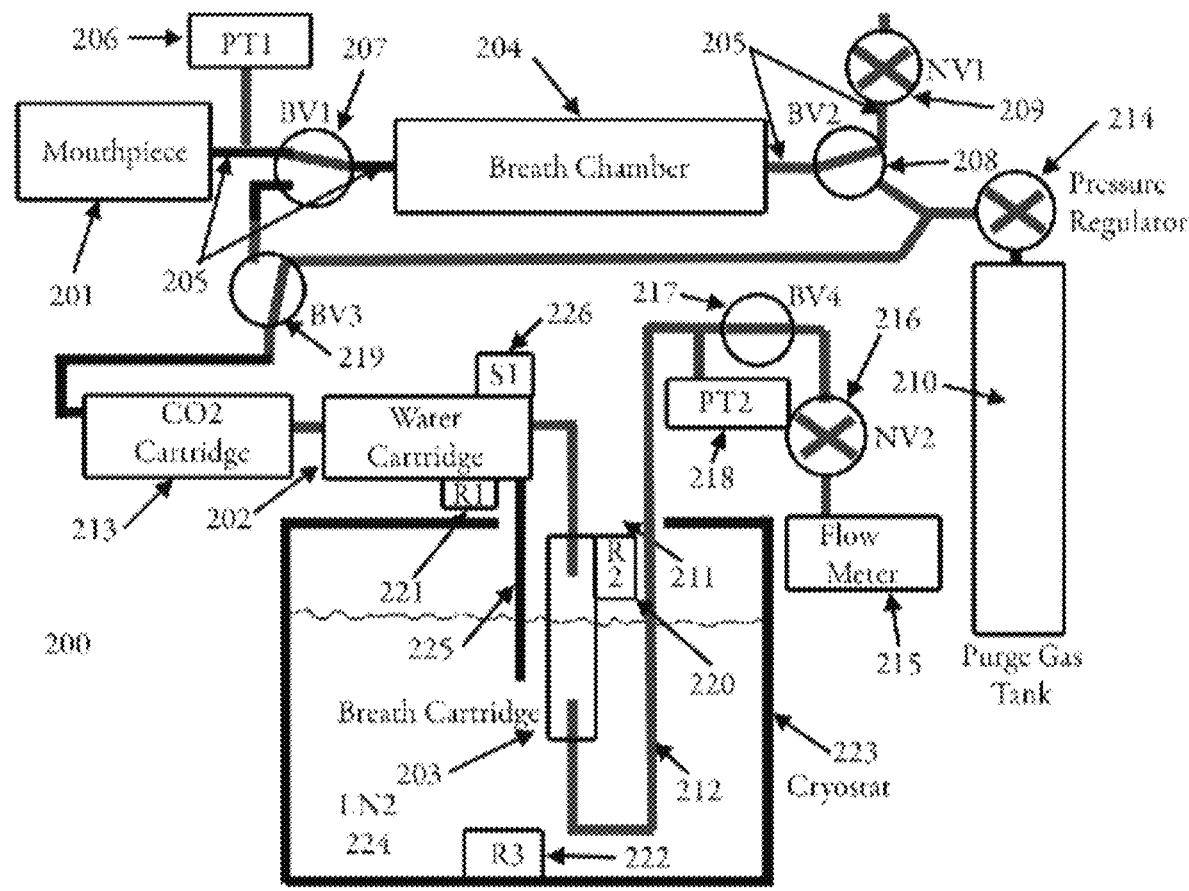
FIG. 2 is a schematic of one embodiment of the disclosed methods, systems, and apparatus.

In the embodiment shown schematically in FIG. 2, system 200 comprises mouthpiece 201, water cartridge 202 for removing water from the captured exhaled breath, breath cartridge 203 for trapping one or more VOCs, and various sensors, valves, and plumbing to direct clean purge gas and exhaled air through system 200. In one embodiment, the subject exhales directly through water cartridge 202 and breath cartridge 203. In a preferred embodiment, the patient exhales into breath chamber 204 that captures a predetermined volume of exhaled air, and subsequently system 200 directs this air through water cartridge 202 and breath cartridge 203 with a predetermined flow rate or flow profile.

Mouth Piece

Mouthpiece 201 can be of any material suitable for contact with the lips and saliva of a subject. Preferred mouthpieces are made of synthetic polymers or cardboard. In one embodiment, mouthpiece 201 is a cardboard tube with an outside diameter in the range of about 23 mm to about 33 mm, preferably about 25 mm to about 30 mm. Preferably cardboard mouthpieces have a white coating to prevent sticking to lips. To reduce the possibility of cross contamination between subjects, mouthpiece 201 is preferably single use disposable and is optionally comprised of a one-way valve (not shown in FIG. 2) that allows exhalation but not inhalation. In one embodiment, system 200 may comprise an adapter that allows for the attachment of a smaller mouthpiece 201 intended for pediatric use. Preferred pediatric mouthpieces 201 have an outside diameter in the range of about 1 mm5 to about 25 mm, preferably about 18 mm to about 20 mm.

Breath Chamber/Breath Capture

Preferably, system 200 comprises breath chamber 204 for capturing a predetermined volume of exhaled air for subsequent transport through breath cartridge 203, preferably through water cartridge 202 followed by breath cartridge 202. Breath chamber 204 can be of any suitable material. Rigid breath chambers 204 are preferably fabricated from metal, such as aluminum or steel, preferably stainless steel. In another embodiment, breath chamber 204 is flexible, and is comprised of a polymeric material, preferably polyvinyl fluoride.

Preferably the assay used to determine the amount of trapped relevant VOCs is sensitive, allowing the amount of air that is captured to be small. Small exhaled air volumes have several benefits, including but not limited to allowing for smaller water cartridges 202 while still avoiding channel blockage from captured water, and less time required to capture exhaled breath. Preferably, system 200 requires less than about 10 exhalations by the subject, less than about 5 exhalations, or less than about 3 exhalations. In a preferred embodiment, system 200 samples air from about 1 exhalation only. Preferably an assay method for the one or more VOCs has a very low limit of quantitation for the one or more VOCs, in order to minimize the required captured air volume. Preferred assay methods include but are not limited to Liquid Chromatography-Mass Spectrometry (LC-MS) and Gas Chromatography-Mass Spectrometry GC-MS.

Preferably, the amount of air sampled from each exhalation is less than or about 4 liters, less than or about 3 liters, less than or about 2 liters, less than or about 1 liter, less than or about 0.5 liters, less than or about 0.4 liters, less than or about 0.3 liters, less than or about 0.2 liters, less than or about 0.1 liters, less than or about 0.05 liters, less than or about 0.025 liters. Preferably the amount of air sampled from each exhalation is in the range of about 0.025 liters to about 1 liter, about 0.05 to about 0.5, or about 0.1 to about 0.2 liters. In one embodiment, about 0.1 or 0.2 liters is sampled from a single exhalation.

Preferably the minimum diameter of any tubing 205 that the subject exhales through, for example between mouthpiece 201 and breath chamber 204, is sufficiently large such that the subject can exhale with minimal effort. Preferably tubing 205 is of minimum inside diameter greater than or about ⅛", greater than or about 3/16", greater than or about 1 U', or greater than or about ⅜". Preferred tubing is about 114" outside diameter, with an inside diameter of about 0.175 or greater, or about ⅜" outside diameter, with an inside diameter of about 0.335 or greater.

In one embodiment, system 200 comprises pressure transducer 206, which has been calibrated to allow for the calculation of exhalation flow rate and exhaled volume through system 200. Preferably the flow resistance of tubing 205 and/or the resistance of resistive element 209 is such that the subject exhales at less than or about 60 Liters Per Minute (LPM), less than or about 45 LPM, less than or about 30 LPM, preferably at about 20 LPM, allowing sufficient time for directional ball valve 207 to be actuated when a target exhalation volume has been reached. Resistive element 209 may be a fixed resistance, or, as shown in FIG. 2, be an adjustable resistance, for example a needle valve. In one embodiment (not shown), prior to reaching the target exhalation volume, the exhalation air can be shunted away from system 200, and when the target exhalation volume has been reached a valve or valves is actuated, directing the exhaled air into breath chamber 204. In the embodiment of FIG. 2, the entire exhalation is directed through breath chamber 204, and when the target exhalation volume has been reached one or more actions occur including but not limited to valve 207 being actuated to block the exhalation flow, a valve, for example ball valve 208, being actuated to isolate breath chamber 204 from the surrounding environment, ball valves 207 and 208 being actuated to direct the contents of breath chamber 204 to water cartridge 202 and/or breath cartridge 203, and/or actuate a direction ball valve (not shown) to shunt the exhalation flow away from breath chamber 204.

In another embodiment, a breath sampling subsystem comprising mouthpiece 201, breath chamber 204, tubing 205, valve 207, valve 208, and resistive element 209 are separate from the rest of breath capture system 200 when the subject exhales through it, and is subsequently attached to the rest of breath capture system 200 for concentration of captured VOCs in breath cartridge 203. Preferably, in this embodiment the breath sampling subsystem is hand held, and weighs less than 5 pounds, preferably less than 2 pounds, more preferably less than one pound. For some disease states, for example neurological conditions like Parkinson's that can make holding a breath sampling subsystem difficult, it may be preferable to mount the breath sampling subsystem on a stand that is attached to or sits on the floor or a piece of furniture such as a table, cart, or chair. The breath capture subsystem may be all mechanical, or have electromechanical valving and/or electronic sensing components such as those described previously.

In some configurations, the breath capture subsystem is all mechanical, and utilizes check valves (not shown) before and after the holding volume of breath chamber 204. Preferably, the check valves require some positive pressure to open (i.e. a positive "cracking pressure") and allow flow, such that when the subject stops exhaling, breath chamber 204 is isolated from the environment, ensuring the captured breath does not escape. These check valves preferably have a cracking pressure of greater than or about 0.25 kPa, greater than or about 0.5 kPa, greater than or about 1 kPa greater than or about 2.5 kPa, greater than or about 5 kPa. Preferably the check valves have a cracking pressure of less than or about 10 kPa, less than or about 7.5 kPa, less than or about 5 kPa, or less than or about 2.5 kPa. The check valves may also prevent the subject from inhaling from the chamber, eliminating the possibility of cross contamination. Preferably the flow resistance of the breath capture subsystem is low enough such that the subject can fully exhale in less than 30 seconds, more preferably in less than 20 seconds, more preferably in less than 10 seconds, more preferably is less than 5 seconds. Preferred flow resistances at an exhalation flow rate of 500 cc/s are less than or about 100 kPa/liter per second, less than or about 50 kPa/LPS, less than or about 40 kPa/LPS, less than or about 30 kPa/LPS, less than or about 20 kPa/LPS, less than or about 15 kPa/LPS, or less than or about 10 kPa/LPS. An example of a suitable check valve is TVCSSVT.125SS (Check-All Valve Mfg. Co., Des Moines, Iowa). Because of the low cracking pressure of these check valves, it may be beneficial to also have ball valves or the like on the input and output of breath chamber 204 which are closed off after the breath sample is gathered to ensure the isolation and purity of the sample.

Figure 12:
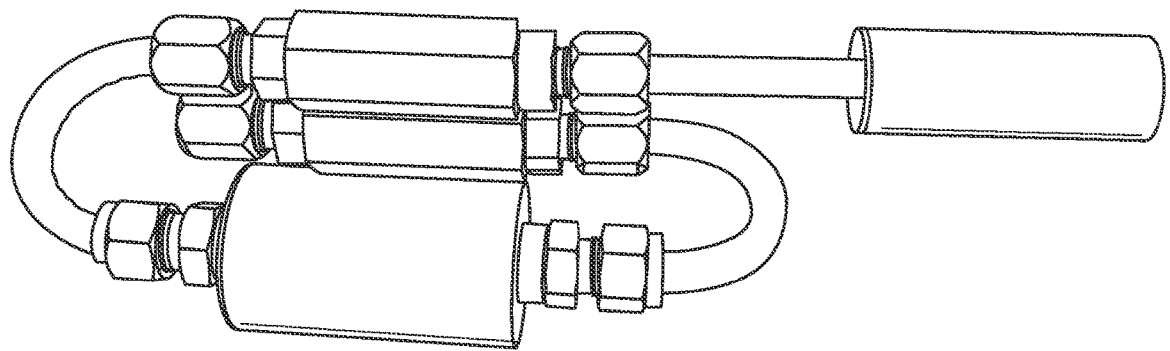
FIG. 12 is a hand-held embodiment of the breath chamber, in accordance with an embodiment.
Figure 13:
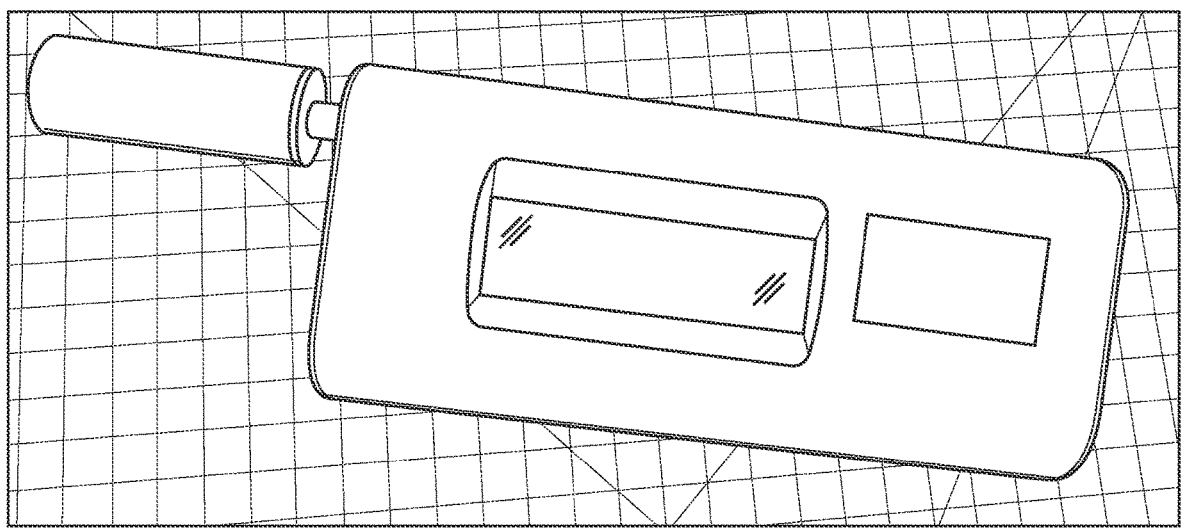
FIG. 13 is the breath chamber embodiment of FIG. 12 in a plastic case, in accordance with an embodiment.

FIG. 12 shows an embodiment of the breath capture subsystem with a 50 ml breath chamber 204. FIG. 13 shows the embodiment of FIG. 12 in a plastic case. Because of the relatively low cracking pressure of the valves required for human exhalation, it is preferable to have another method of closing off breath chamber 204 ends after the exhalation, as during the handling and transport the check valves may open due to acceleration or vibration. For example, after exhalation, the input and output of breath chamber 204 maybe blocked by a mechanism including but not limited to plugs, stoppers and the like, or valves, for example ball valves.

For some applications, it is preferable to capture breath from a preselected region of the lungs. Capture of exhaled VOCs could be used for the early detection of lung cancer and other lung diseases. In this case it may be preferable to capture air from the region of lung where the morbidity is expected to occur, for example the more central airways. Other applications may require the detection of VOCs that are generated in other regions of the body and then delivered to the lungs via the systemic circulation. Thus, in some configurations, it may be preferred to ensure that the sample is captured from air after a predetermined volume of air has been exhaled, as the first air exhaled from the lungs is mostly made up of the last air inhaled, which has mostly resided in the mouth and more central airways and thus has not equilibrated with the systemic circulation. The volume of air from the mouth and central, conducting airways that may have not fully equilibrated with the systemic circulation (the "anatomic dead space") averages about 150 ml in humans.

Figure 3:
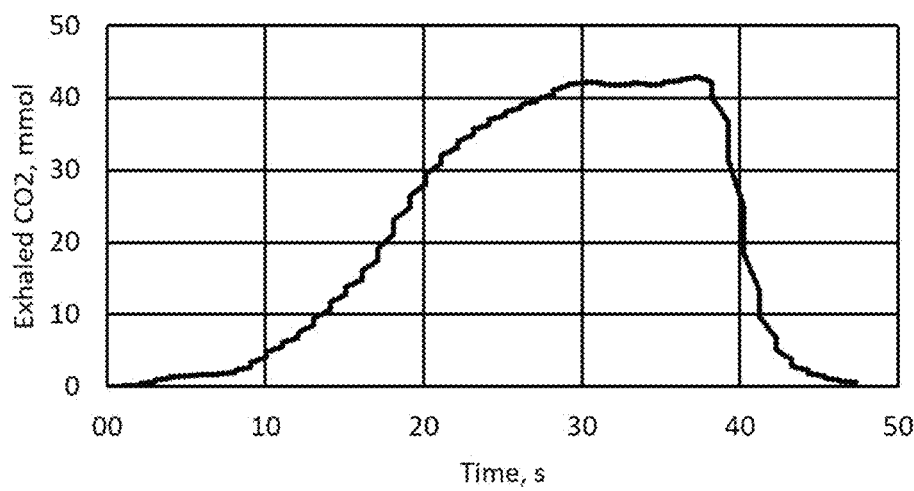
FIG. 3 is a measurement of exhaled CO2 in breath, in accordance with an embodiment.

One way to determine if exhaled air has originated from the lung periphery and has equilibrated with the systemic circulation is to measure the amount of CO2 in the exhaled air. FIG. 3 shows such a measurement of exhaled CO2 as a function of time. The exhalation flow rate was approximately 0.4 LPM, as controlled by watching a flow meter while exhaling. It can be seen that initially the CO2 levels were very low, climbing to about 42 mmol at about 30 seconds which corresponds to about 0.2 liters. The rise in CO2 levels is likely due to air originating in the central airways mixing with increasingly large fractions of air from the lung periphery. After about 0.2 liters are exhaled, the amount of exhaled CO2 essentially levels off, suggesting that this air is now coming essentially completely from the lung periphery and is in equilibrium with the systemic circulation. The value of about 0.2 liters is in good agreement with the expected anatomic dead space volume of 150 ml.

In one embodiment, when air in equilibrium with the systemic circulation is desired, CO2 is monitored, and the measured amount of exhaled CO2, or the slope of the CO2 vs. time or CO2 vs. exhaled volume curve as described above is used to determine when to start sampling air for VOC capture. In another embodiment, air is exhaled for a predetermined amount of time prior to sampling air for VOC capture. In a preferred embodiment, a preselected volume of air, as measured by integrating the signal from pressure transducer 206 which has been previously calibrated for exhaled volume as a function of exhalation pressure, is exhaled before beginning the sampling of air for VOC capture. Preferably the amount of the selected volume is greater than or about equal to the maximum anatomic dead space volume expected in the subject population. Preferably the predetermined volume is greater than or about 150 ml, greater than or about 200 ml, greater than or about 300 ml, greater than or about 500 ml, greater than or about 750 ml, or greater than or about 1 liter.

Although as described below, the removal of water and the collection of VOCs is optimized by reducing the temperature to the point that the exhaled water, VOC, or VOCs are saturated, there can be some VOCs bound to the surface at any temperature. Therefore, it is preferable to minimize the internal surface area that the captured exhaled breath is exposed to. This may be most relevant in breath chamber 204, because of the long residence time of the captured exhaled air. Preferably the internal surface area of breath chamber 204 is less than or about 500 $cm^2$, less than or about 400 $cm^2$, less than or about 300 $cm^2$, less than or about 200 $cm^2$ or less than or about 150 $cm^2$, or less than or about 125 $cm^2$. One embodiment of breath chamber 204 is a shape that is essentially spherical, as a sphere has the smallest possible surface to volume ratio. By way of example, a spherical 100 ml sphere has a surface area of just 104.2 $cm^2$, and a 200 ml sphere has a surface area of 165.4 $cm^2$. One embodiment of breath chamber 204 is a tube of relatively large outside diameter. In this embodiment, it is relatively straightforward to adjust breath chamber 204 volume by using different lengths of tube. Preferably the tube outside diameter is selected from a list including but not limited to ¾", ⅞", 1", 1¼", 1 $W^{1/2}$ or 2 inch, or readily available metric equivalents. Preferably the combined internal surface area of mouthpiece 201, tubing 205, valves 207 and 208, and breath chamber 204 are less than or about 100 $cm^2$, less than or about 800 $cm^2$, less than or about 600 $cm^2$, less than or about 400 $cm^2$ or less than or about 300 $cm^2$, or less than or about 150 $cm^2$.

The tubing sizes for breath chamber 204 described above are preferred because compression fittings, for example Swagelok fittings, are readily available for adapting the tubing to smaller tubing for connecting to mouthpieces, valves, etc. One particularly preferred diameter is about 2", because it has a minimal surface to volume ratio. By way of example, one readily available size of stainless-steel tubing has an about 2" outside diameter and about 0.065" wall thickness, yielding an inside diameter of about 1.87". For the example of a 100 ml breath chamber, the total surface area, including end caps, is about 119.7 cm$^2$, only about 15% more than the sphere of equal volume. A 200 ml breath chamber would have a surface area of 203.9 cm$^2$ somewhat larger than the equivalent sphere. For volumes of about 50 ml or less, the combined area of the 2" endcaps start to dominate the surface area, and a smaller tube, for example 1.5", will have a lower surface area for the same volume. Preferably breath chamber 204 captures less than or about 50%, less than or about 10%, less than or about 5%, less than or about 2%, less than or about 1%, or less than or about 0.5% of the one or more VOCs of interest.

Figure 7:
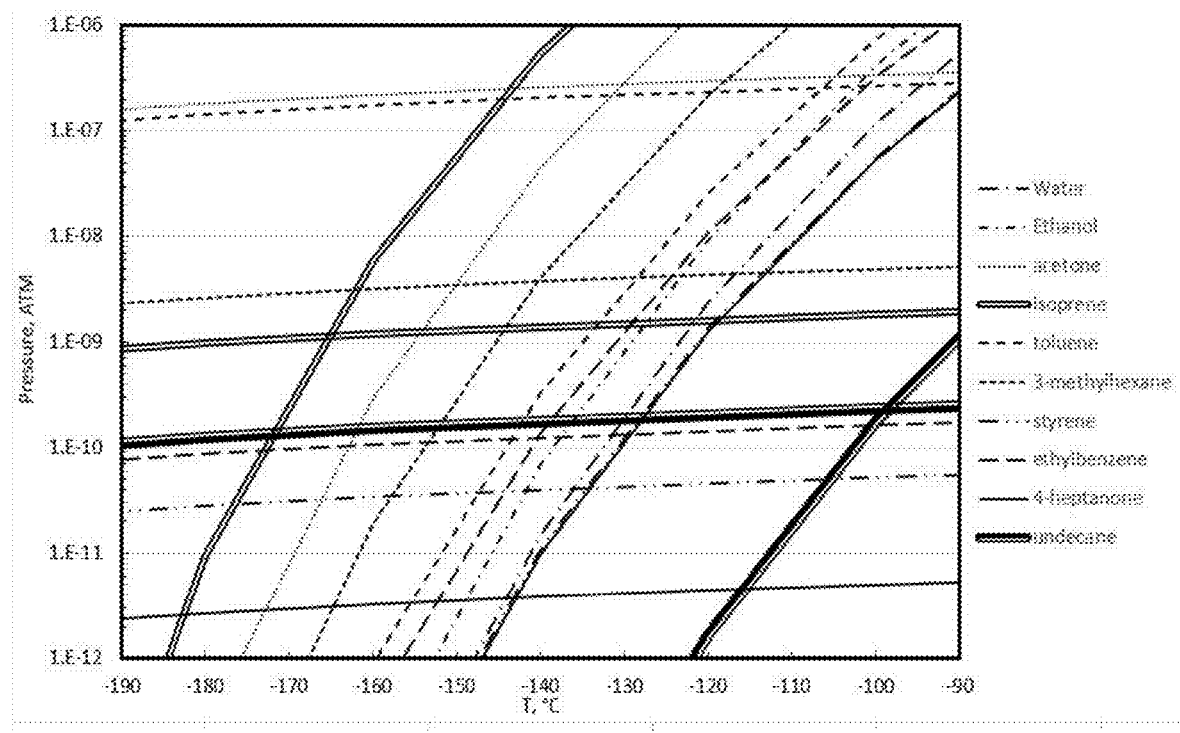
FIG. 7 is a graph of saturated vapor pressure and expected vapor pressure of various VOCs in exhaled air as a function of temperature, in accordance with an embodiment.

Preferably, the breath that is captured is not contaminated by VOCs in the inhaled air. One way to minimize this is to have the subject breath in uncontaminated air, either from a source of clean air, or from air that has been run through a cartridge similar to breath cartridge 203 described in more detail below to remove any VOC contaminants. A preferred way of removing VOCs in the inhaled air is to have the subject hold their breath for a period of time that allows the VOCs to travel to and be absorbed by the wall of an alveolus in the lung, ensuring that the air is in equilibrium with the systemic circulation and any VOCs from the inhaled air are removed from the air by the lung. By way of example, the VOC from FIG. 7 with the highest molecular weight, and thus the lowest diffusion coefficient is undecane, with a molecular weight of 156.31 gmol$^{-1}$ and an estimated diffusion coefficient at body temperature of 0.085 cm$^2$/s. The root mean square distance an undecane molecule will diffuse in a time t is $(6Dt)^{1/2}$. The average diameter of a human respiratory bronchiole is about 500 microns, or 0.05 cm. The time for an average undecane molecule to diffuse 500 microns is $(0.05\ \text{cm})^2/(6*0.085\ \text{cm}^2/\text{s})=4.9\times10^{-3}$ seconds. Thus, with a very short breath hold of about 1 second it can be seen that the air in the alveolar region will be fully equilibrated with the lung, and should not be impacted by any VOCs in the inhaled air. One may wish to sample air from the more central airways, for example to diagnose certain lung diseases like cancer, asthma, COPD, and the like, the distance a molecule will diffuse perpendicular to the axis of a substantially cylindrical airway is given by $(4\ Dt)^5$. For a bronchial airway of diameter approximately 0.5 cm, the RMS time for an undecane molecule to diffuse the diameter of the airway is about 0.74 seconds. So for the embodiment where one wishes to sample air from the bronchial airways, a few second breath-hold will bring the inhaled air into equilibrium with the airway walls.

Transport of Captured Breath

Preferably, after the capturing of the predetermined amount of exhaled air in breath chamber 204, the captured breath is drawn through water cartridge 202 and subsequently through breath cartridge 203. This can be accomplished by the use of a vacuum pump (not shown). It is preferable that no outside air mixes with the captured exhaled air so that the sample is not contaminated with environmental VOCs. This can be accomplished by using a flexible polymeric bag to capture the exhaled air, and then allowing the bag to collapse when the air is pumped out. Similarly, one could capture the air in a tube with a sealing piston which travels down the tube due to the force created by the reduced pressure in the tube caused by the vacuum pump. Alternatively, the air could be forced out of breath chamber 204 under positive pressure. This could be done with a cylinder and piston as described above, wherein the piston is positively displaced, for example by a linear actuating mechanical device or by positive air pressure. This could also be done by placing the polymeric container in a second, airtight container and pressurizing the second container. These concepts have the advantage that they minimize the time that captured gas flows through the water and breath cartridges because the gas is not diluted by any other gas. However, these concepts may not be preferred because they have moving parts, and polymer bags or seals that may outgas VOCs.

Alternatively, the captured air could be forced out of breath chamber 204 by introducing clean, preferably inert, purge gas from purge gas tank 210 into breath chamber 204 as shown in FIG. 2. Preferred gasses include but are not limited to argon, xenon, or krypton, preferably nitrogen hydrogen, or neon, most preferably helium. Preferably any impurities in the gas are at levels less than or about 100, less than or about 10, or less than or about 1 part per billion (PPB) and any VOCs of interest are at levels such that the amount of each VOC contained in the total amount of purge gas drawn through breath cartridge 203 is less than about 10%, less than about 1%, or less than 0.1% of the total amount expected in the captured volume of exhaled air. Preferably the dimensions of breath chamber 204 and the gas flow rate are such that the flow through breath chamber 204 is expected to be laminar (i.e. Reynolds number less than or about 2000), minimizing mixing with purge gas. Preferably the volume of purge gas that flows through breath chamber 204 is greater in volume than the volume of breath chamber 204 such that a large fraction, greater than or about 90%, greater than or about 99%, or greater than or about 99.9% of the captured breath is delivered to breath cartridge 203. Preferably the volume of purge gas is more than or about 1.5×, more than or about 2×, more than or about 3×, more than or about 5×, more than or about 10×, or more than or about 20× the volume of breath chamber 204.

Similar to breath chamber 204, the total surface area of all surfaces the exhaled breath contacts prior to introduction into the breath cartridge 203 is preferably minimized. Also, the cross-sectional area should be minimized to minimize residence times. Preferably the total surface area of all breath contact surfaces prior to the breath cartridge 203 should be kept less than or about 200 cm$^2$, less than or about 150 cm$^2$, less than or about 100 cm$^2$, less than or about 75 cm$^2$, or less than or about 50 cm$^2$. Preferably the tubing that the subject exhales through is about ¼" or about ³⁄₁₆" OD (or readily available metric equivalent) stainless steel tubing, as smaller sizes will create an elevated high pressure drop and exhalation times will be uncomfortably long, and larger sizes will have higher surface area and longer residence time than necessary. In embodiments where the subject does not exhale directly through water cartridge 202 and/or breath cartridge 203, the tubing used should in general be smaller, as higher pressures will be available, and in general longer flow times will be used to optimize performance of the water and/or breath cartridge 203. Smaller tubing is also preferred because in addition to presenting a smaller surface area and residence time, it minimizes heat conduction to the VOC and water cartridges. About ³⁄₁₆", about ⅛", or about ⅛" OD (or readily available metric equivalent) stainless steel tubing is preferred. Preferably the surfaces before the breath cartridge 203 capture less than or about 50%, less than or about 10%, less than or about 5%, less than or about 2%, less than or about 1%, or less than or about 0.5% of the one or more VOCs of interest.

Water Cartridge

Figure 4:
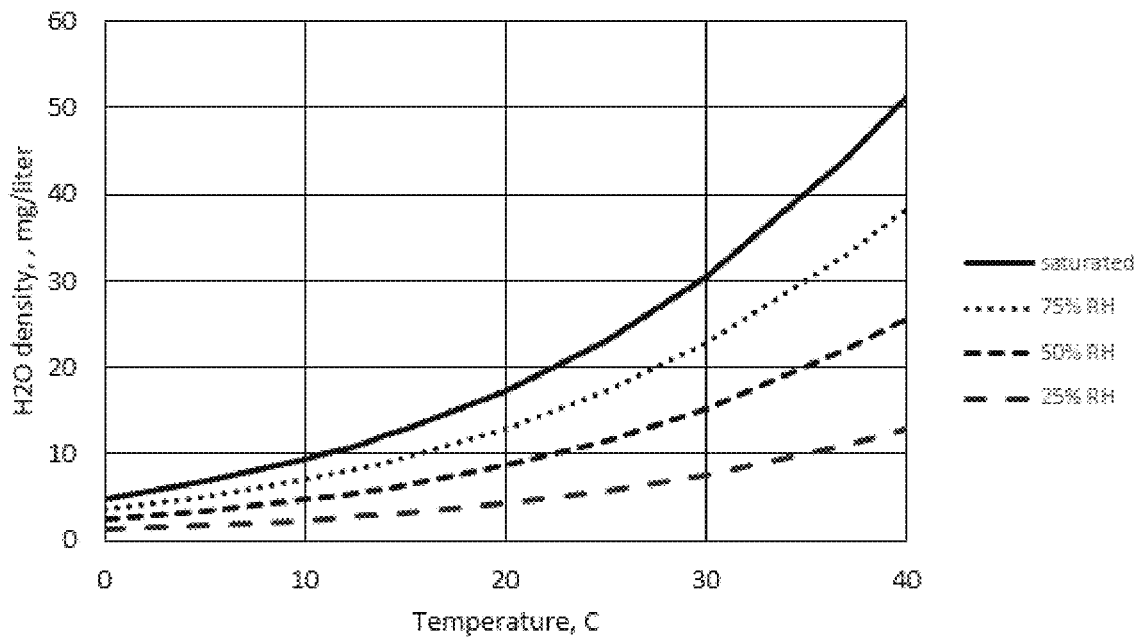
FIG. 4 is a graph of water vapor content in air as a function of temperature above 0° C., in accordance with an embodiment.

Water cartridge 202 may remove water from the captured air in order that that the water not interfere with the assay of the VOCs, and so that the water does not damage one or more components of the assay apparatus, for example components selected from the group including but not limited to a gas chromatography column and a liquid chromatography column. A human exhales air that is saturated (or possibly supersaturated) with water at a temperature of about 34° C. FIG. 4 shows the amount of water vapor in air as a function of temperature at 25%, 50%, 75%, and 100% relative humidity. It can be seen from FIG. 4 that a person, exhaling at 34° C. and 100% relative humidity, will exhale about 38 mg of water vapor per liter of air. In the case where 100 ml of exhaled air is captured, it will initially contain at least 3.8 mg of water, although while the air is in breath chamber 204 and tubing some of the water will condense out on the walls, which are in general at a temperature below 34° C. Preferably after passing through water cartridge 202, the captured air contains less than about 100 µg, less than about 10 µg, less than about 1 µg, or less than about 0.1 µg of water. Preferably about 90% or more, about 99% or more, about 99.9% or more, or about 99.99% or more of the water is removed by water cartridge 202.

Preferably water cartridge 202 is cooled to a temperature such that when the air equilibrates with the walls of water cartridge 202 the remaining water vapor is at or below a desired level. One preferred maximum amount of water vapor in the captured air when introduced to breath cartridge 203 is 8.3 µg. This corresponds to 1 percent water vapor when the collected VOCs are dispersed into 5 ml of an inert gas such as but not limited to helium gas for introduction into a gas chromatography column. By way of example it can be assumed that about 100 ml of air is captured. In this case, a total water vapor mass of 8.3 µg would correspond to 83 µg/liter. As can be seen from FIG. 4, saturated air at 0° C. has about 5 mg of water per liter of air, about 60× the target amount. One can see that if the water in 100 ml of exhaled air is to be lowered to 8.3 µg, the temperature must be lower than 0° C. In this case, the captured water will be frozen, and determination of the required temperature requires calculation of the amount of water vapor that sublimates from water ice as a function of temperature. For this calculation, the following expression (Wexler, JOURNAL OF RESEARCH of the National Bureau of Standards-A. Physics and Chemistry, 81A(1),) 1977, after correction of temperatures from IPTS-68 to ITS-90) can be used:

$$\ln(P/P_t) = (a_1\tau + a_2\tau^2 + a_3\tau^3 + a_4\tau^4)T_t/T$$

where p is the pressure, T is the temperature, the subscript t refers to the triple point, $\tau \equiv 1-T/T_t$, $T_t=273.16$ K, $p_t=611.657$ Pa, $a_1=-22.4948$, $a_2=-0.227$, $a_3=0.502$, $a_4=0.562$. The following table tabulates the vapor pressure of water P in Pascal (Pa) at a temperature t in Celsius:

| t/° C. | | | | | | | | | | |
|---|---|---|---|---|---|---|---|---|---|---|
| | −100 | −90 | −80 | −70 | −60 | −50 | −40 | −30 | −20 | −10 |
| p/PA | 0.0014 | 0.0097 | 0.055 | 0.261 | 1.080 | 3.94 | 12.84 | 38.00 | 103.2 | 259.9 |

Figure 5:
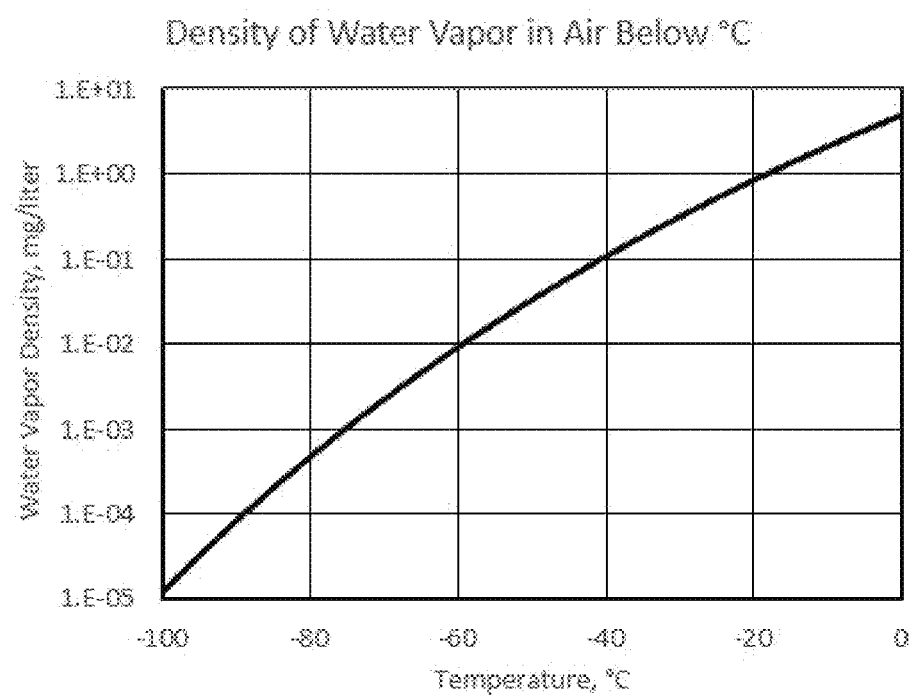
FIG. 5 is a graph of water vapor content in air in equilibrium with water ice as a function of temperature below 0° C., in accordance with an embodiment.

FIG. 5 is a graph of water vapor density of air in equilibrium with ice at temperatures from about 0 to −100° C. calculated using the expression above. It can be seen that to achieve a target water vapor density of less than 83 µg/liter, a temperature of less than or about −45° C. must be used.

Preferably the temperature of water cartridge 202 is less than or about 0° C., less than or about −10° C., less than or about −20° C., less than or about −30° C., less than or about −40° C., less than or about −50° C., less than or about −60° C., less than or about −70° C., less than or about −80° C., less than or about −90° C., or less than or about −100° C. One particularly preferred temperature is about −55±5° C.

Figure 6:
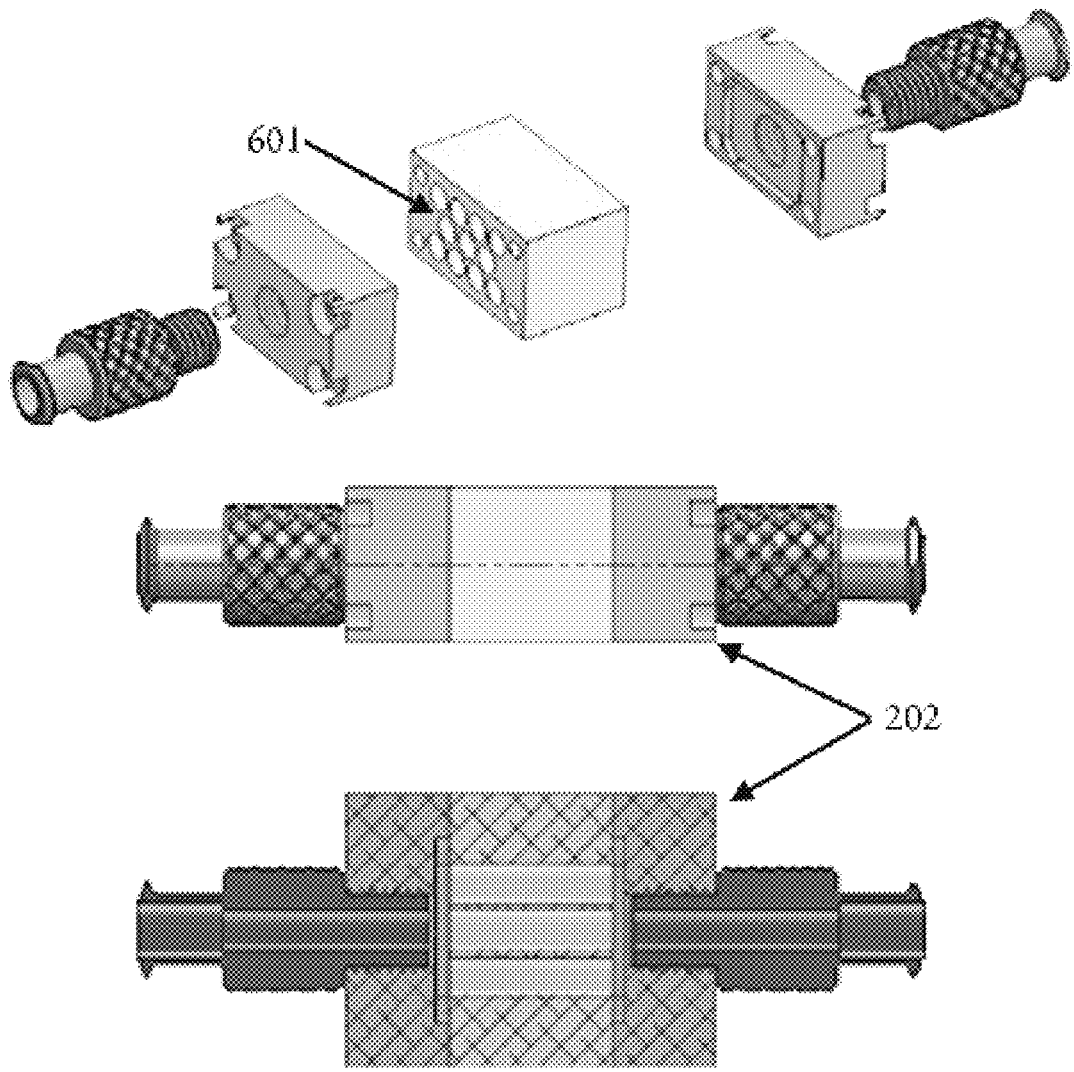
FIG. 6 is a drawing of one embodiment of the water cartridge of the disclosed methods, systems, and apparatus, in accordance with an embodiment.

FIG. 6 shows one possible embodiment of a water cartridge with 11 channels 601.

In addition to the temperature requirement, it also may be required that the dimensions of the channel or channels 601 of water cartridge 202 and the rate of flow through water cartridge 202 must be such that the required trapped fraction of water can diffuse to the walls of channels 601 of water cartridge 202 during the residence time of the captured breath in water cartridge 202. Assuming a temperature dependence of $T^{1.5}$, the diffusion coefficient of water can be estimated as $D=0.21*(T/298.12)^{1.5}$ where the diffusion coefficient of water at 25° C. is 0.21 cm²/s and T is in degrees Kelvin. Knowing the diffusion coefficient, a person skilled in the art can calculate the dimensionless diffusion parameter $\mu=\pi DL/Q$, where L is the length of a water cartridge channel 601, and Q is the volumetric air flow rate.

Using the calculated diffusion parameter µ, the capture efficiency in percent can be calculated using the following formula as adapted from Baron and Willeke (B&W) Aerosol Measurement, 2nd Edition, J Wiley and Sons, 2001:

$$[1-0.81905*e^{-3.6568*\mu}+0.09753*e^{-22.305*\mu}+0.0325*e^{-56.961*\mu}+0.01544*e^{-107.62*\mu}]*100$$

Because the above expression only depends on µ, one can see that the capture efficiency only depends on D, L, and Q. Because D is proportional to $T^{1.5}$ where T is in Kelvin, the capture efficiency can be characterized by $L*T^{1.5}/Q$. One can calculate that if a capture efficiency greater than 90% is desired, $L*T^{1.5}/Q>C*10000$, where C=5.0, L is in cm, and Q is in liters per minute. If a capture efficiency of greater than 99% is desired, C=11. If a capture efficiency of greater than 99.9% is desired, C=16. If a capture efficiency of greater than 99.99% is desired, C=21. Of course, to achieve these collection efficiencies, a sufficiently low temperature must be used, as discussed above.

One can see that the collection of water at a fixed volumetric flow rate in a channel is independent of the channel diameter d, as for a given length and volumetric flow rate, the residence time increases as d², but the distance molecules diffuse on average scales as $t^{1/2}$ (where t is time). Given that a water molecule must diffuse a distance of order d in order to hit a wall, one can see that increasing the diameter increases the residence time by exactly the factor required to give sufficient time for the molecule to diffuse by the increased diameter. By way of example, if the diameter of a water cartridge channel were to double, the residence time would increase by a factor of about 4, resulting in an increase of diffusion distance of a factor of about 2, equal to the doubled diameter.

Another interesting result is that if multiple channels are used in parallel, the length L to be used in the calculation of µ is the sum of the lengths of the channels. This can be understood from the following example: If a given channel of length L resulted in a capture efficiency of C %, using instead n channels of length L/n would result in 1/n of the volumetric flow rate in each channel, implying a residence time in each l/n length channel equal to the original residence time of the full length channel. Thus the water molecules have the same amount of time to diffuse across a channel of the same diameter, resulting in the same capture efficiency C.

In one embodiment, it is desired to capture 99.9% of the water vapor in 100 ml of exhaled air in water cartridge 202. Using the information above, this can be accomplished by transporting the air at a flow rate of about 0.4 LPM through water cartridge 202 held at a temperature of about −45° C., wherein water cartridge 202 is comprised of 8 channels of length about 2.5 cm.

Water cartridge 202 can be cooled by any means, including but not limited to a standard refrigerator and a Peltier thermoelectric cooler (TEC). Preferred TEC embodiments include but are not limited to one or more 2 stage TECs, one or more 3 stage TECs or one or more TECs with greater than 3 stages.

In a preferred embodiment water cartridge 202 is cooled using a cryogenic liquid, preferably liquid nitrogen (LN2) 224. Because the temperature of LN2 224 at atmospheric pressure is −196° C. (77° K), in general water cartridge 202 will not be submerged in LN2 224. In one embodiment, water cartridge 202 is cooled by the gas that is released when LN2 224 evaporates or boils. This cooling can be increased by the use of resistor R3 222 which is submerged in liquid nitrogen 224. Preferred resistors R3 222 include but are not limited to 25Ω or 50 Ω, 10, 25, 50, 75, or 100 watt power resistors. Alternatively, or in addition, water cartridge 202 may be cooled by cold finger 225 that extends into liquid nitrogen 224. Preferably cold finger 225 is comprised of a metal, preferably selected from the list including but not limited to copper, aluminum, steel, and stainless steel, combinations thereof, or the like. Preferably cold finger 225 is a rod of diameter greater than or equal to about 1/16", greater than or equal to about 1/8", greater than or equal about 3/16", or greater than or equal to about 1/4". Although rods of circular cross section are preferred, any shape cross section of equivalent cross-sectional area can be used. Preferred cross-sectional areas are greater than or about 0.0031 square inches, greater than or about 0.0123 square inches, greater than or about 0.0276 square inches, or greater than or about 0.0491 square inches.

The temperature of water cartridge 202 can be controlled without closed loop control by controlling the dimensions of cold finger 225, the heat delivered to submerged power resistor R3 222, heat delivered to power resistor R1 221 mounted on water cartridge 202, or the current delivered to a TEC (not shown). However, these methods have the disadvantage that the temperature of water cartridge 202 will vary with the height of liquid nitrogen 224, the amount of heat load on LN2 bath 224 and therefore the rate of boil off of LN2 224, and the heat load on water cartridge 202. In a preferred embodiment, the temperature of water cartridge 202 is closed loop servo controlled. Any suitable control methodology can be used, including but not limited to a methodology selected from the list of proportional, Proportional Integral Differential (PID), and Model Referenced Adaptive Control (MRAC). Preferably, the servo controls the temperature of temperature sensor 226 which is in intimate thermal contact with water cartridge 202. Temperature sensor 225 can be any suitable temperature sensor technology, including but not limited to a resistor, a thermocouple, but is preferably a silicon diode. Preferably the servo controls the temperature by a method selected from but not limited to heating resistor 226 that is in contact with water cartridge 202, heating and/or cooling water cartridge 202 with one or more TECs (not shown) that are in contact with water cartridge 202, and/or controlling the current to power resistor R3 222 that is submerged in liquid nitrogen 224. Preferably power resistor R1 221 is attached to water cartridge 202 close to cold finger 225, if cold finger 225 is used, and temperature sensor 226 is also located close to cold finger 225. This will minimize temperature gradients across water cartridge 202. Preferably any temperature difference at two points on water cartridge 202 is less than or about 10° C., less than or about 7.5° C., less than or about 5° C., less than or about 2.5° C., or less than or about 1° C.

In some embodiments, water cartridge 202 is precooled, for example before system 200 has a complete fill of liquid nitrogen 224. Water cartridge 202 may be precooled by a method including but not limited to storing it in a freezer, immersing it in a cryogenic fluid, preferably liquid nitrogen, or cooling it with one or more TECs. Preferably water cartridge 202 is precooled by filling cryostat 223 with cryogenic fluid 224 (for example into which a breath cartridge 203 will be submerged), preferably LN2 224, by pouring cryogenic fluid 224 over water cartridge 202. This can be done by having a two-stage cryostat 223 with water cartridge 202 in an upper stage, and a lower stage which contains cryogenic fluid 224. The two stages can be connected by passage 211 through which cryogenic fluid 224 drains from the upper stage into the lower stage when cryogenic fluid 224 is poured over water cartridge 202. The passage is also useful as a conduit for directing cooled nitrogen gas from LN2 224 boil off over water cartridge 202 for cooling. The passage can also be used for cold finger 225 from water cartridge 202 to LN2 224, and for tubing to conduct the captured air from water cartridge 202 to a breath cartridge 203 which is at least partly submerged in LN2 224, and snorkel 212 which is comprised of tubing for directing the air that has passed through the water cartridge 202 and breath cartridge 203 out of LN2 224, and/or mechanism 1100 for actuating one or more valves on the breath cartridge 203 (e.g., FIG. 11), preferably when breath cartridge 203 is still submerged in LN2 224.

Similar to breath chamber 204, it is preferable to minimize the surface area of water cartridge 202 exposed to the captured breath in order to minimize the loss of VOCs. Therefore, although the trapping of water is independent of the diameter of water cartridge channels 601, it is preferable to minimize the diameter to minimize the surface area exposed to the VOCs. Using circular cross section channels 601 is preferred because a circular channel 601 has the minimum exposed surface area for a given cross sectional area, pressure drop, etc. Preferably water cartridge 202 captures less than or about 50%, less than or about 10%, less than or about 5%, less than or about 2%, less than or about 1%, or less than or about 0.5% of the one or more VOCs of interest.

Another feature in the embodiments is that the water trapped by water cartridge 202 does not block the flow of air. In general, water cartridge 202 will be maintained at a temperature below 0° C., and thus the water will be trapped in the form of ice. As discussed above, the captured breath will contain as much as about 3.8 mg of water per 100 ml of breath captured, which has an ice volume of at least about 4.07 µl per 100 ml of breath captured. Thus it is important that the volume of the channel or channels 601 in water cartridge 202 be more than about 4 µl per 100 ml of exhaled breath captured. However, it is preferred that water cartridge 202 have high captured efficiency, for example trapping about 99.9% of the water. In this case, where water cartridge 202 is comprised of one or more cylindrical channels 601, the first 1/3 of water cartridge 202 channel(s) 601 will trap about 90% of the water, the second ⅓ will capture about 9% of the water and the third ⅓ will capture about 0.9% of the water. Thus the volume of the first ⅓ of the water cartridge channels 601 should be more than 0.9*4.07 µl or 3.66 µl, implying a water cartridge volume of more than or about 11 µl. Still larger volume water cartridges are preferred because the water will deposit preferentially in the upstream section of the first ⅓, for example larger than or about 12.5 µl, larger than or about 15 µl, larger than or about 17.5 µl, or larger than or about 20 µl.

Preferred water cartridge channels 601 have a volume of more than or about 10 µl, more than or about 25 µl, or more than or about 50 µl, per 100 ml of air captured. Preferably water cartridge 202 channel volume is more than or about 3 times, more than or about 6 times, more than or about 10 times, or more than or about 20 times the expected amount of water to be captured. In the case where VOC deposition is to be minimized and thus the surface area of water cartridge 202 is to be minimized, tapered, for example conical, channels can be used. Preferably the taper is such that the volume of the first ⅓ of water cartridge 202 has a volume greater than or about 3.66 µl, the second ⅓ has a volume greater than or about 0.366 µl, and the third ⅓ has a volume greater than or about 0.0336 µl per 100 ml of captured breath.

Water can also be removed using a process that also removes CO2, such as a molecular sieve, see below.

Carbon Dioxide Cartridge.

In addition to removal of water, it can be beneficial for reducing pressure and improving assay performance, to remove carbon dioxide using CO2 cartridge 213. Carbon dioxide can be removed by any of a number of methods, including but limited to molecular sieves, amine scrubbing minerals and zeoplies, including but not limited to sodium hydroxide and lithium hydroxide, activated carbon, metal organic frameworks, adsorption optionally at reduced temperatures, bioreactors, and reversing heat exchanges.

In one embodiment, CO2 cartridge 213 comprises a molecular sieve. Preferably, the molecular sieve has a pore diameter selected to remove water and CO2, but to minimize the loss of larger VOCs. Preferred pore diameters include greater than or about 1 angstrom, greater than or about 2 angstroms, greater than or about 3 angstroms, greater than or about 4 angstroms, or greater than or about 5 angstroms.

Figure 14:
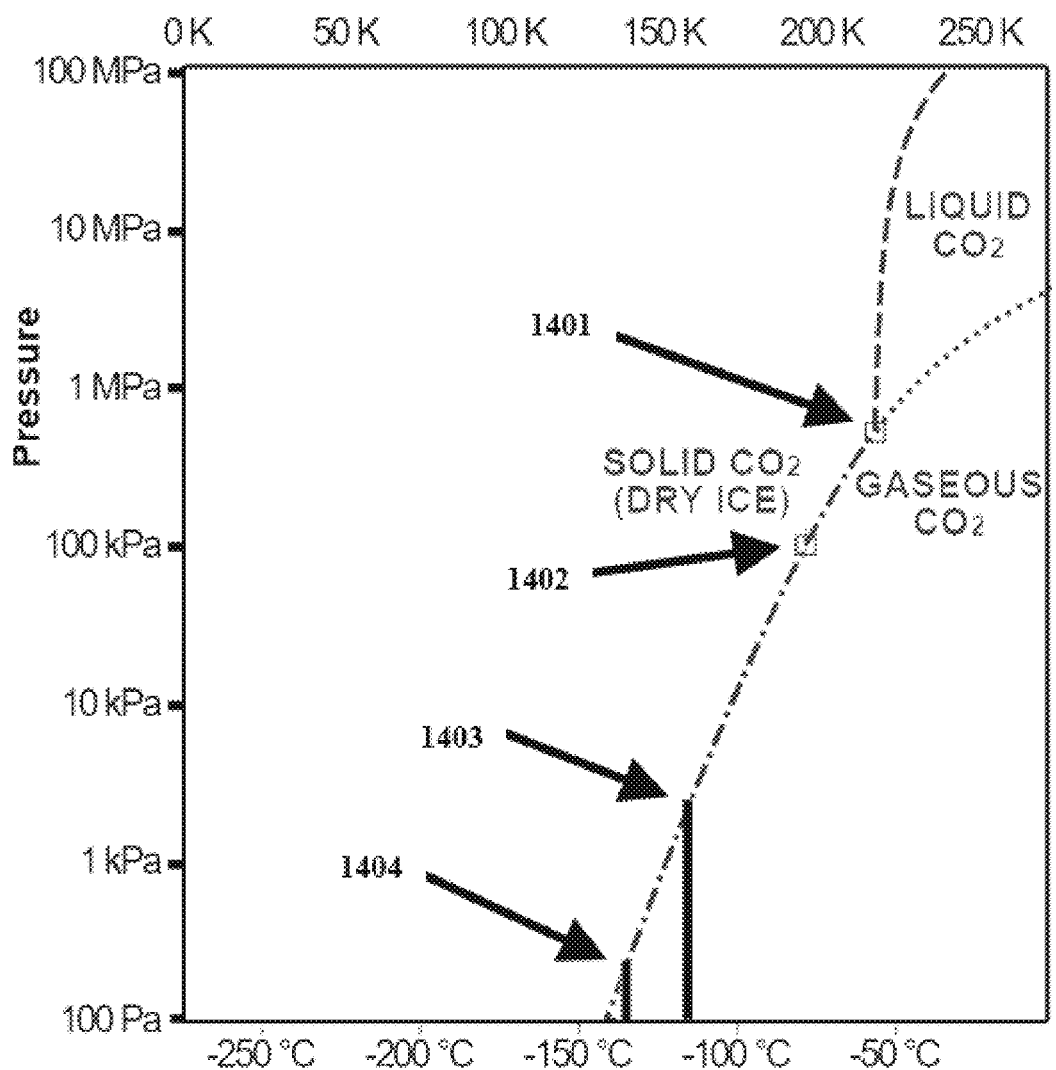
FIG. 14 is a phase diagram of CO2, indicating temperatures at which CO2 starts to be removed from exhaled air, and the temperature at which 90% of CO2 is removed, in accordance with an embodiment.

Alternatively, CO2 can be removed using a system similar to water cartridge 202 described above. FIG. 14 shows a phase diagram of CO2. Triple point 1401 is the point at −56.6° C. and 518 kPa where liquid, solid, and gaseous phases of CO2 coexist. CO2 sublimation point 1402 is where solid and gaseous phases of CO2 are in equilibrium at one atmosphere, at −78.5° C. At the concentration of CO2 in end tidal exhaled air, CO2 saturation point 1403 at about −115° C., or about −114 to about −116° C., or about −112 to about −118° C., or about −110 to about −120° C., is where CO2 starts to be removed from exhaled air, and 90% removal point 1404 is where 90% of CO2 is removed when in equilibrium with a surface at about −135 C, or about −134 to about −136° C. or about −132 to about −138° C., or about −130 to about −140° C. In order to minimize the amount of VOCs that are lost to CO2 cartridge 213, the following process can be used: First, capture 90% of the CO2 by cooling CO2 cartridge 213 to 90% removal point 1404. Air and VOCs that pass through CO2 cartridge 213 are then passed through a breath cartridge 203 (see below) wherein remaining VOCs are captured and concentrated. Purge gas is then caused to flow through CO2 cartridge and then shunted away before reaching breath cartridge 203 while the temperature of CO2 cartridge 213 is increased to CO2 saturation point 1403, during which the CO2 is returned to the gas phase and removed. Subsequently, flow of the purge gas through the breath cartridge 203 is restored, and the temperature of CO2 cartridge 213 is increased to more than or about −100°, whereby the VOCs that were previously captured by CO2 cartridge 213 at temperatures above CO2 saturation point 1403 are released from CO2 cartridge 203 and are captured by breath cartridge 203.

Many of the methods for capturing CO2, including molecular sieve and low temperature adsorption, will capture water also, obviating the need for separate CO2 cartridge 203 and water cartridge 202.

Breath Cartridge

After the air has optionally passed through CO2 cartridge 213 and/or water cartridge 202, it is preferably directed to breath cartridge 203. There are many VOCs of potential interest in exhaled breath, some of which are included in FIG. 7. Exhaled VOCs are generally comprised of constituents including but not limited to multiple carbon and hydrogen atoms, and may also include oxygen, nitrogen, and sulfur.

Breath cartridge 203 can be comprised of an absorbing medium, and can be held at a reduced temperature, for example less than or about 0° C., less than or about −20° C., less than or about −40° C., less than or about −60° C., less than or about −80° C., or less than or about −100° C. The temperature can be achieved and controlled using any of the methods described above for water cartridge 202. At these temperatures, capture efficiencies of VOCs are generally low, which leads to high variability, as discussed above in reference to FIG. 1. This method in general also requires high surface areas, and heating to release the VOCs.

Figure 8:
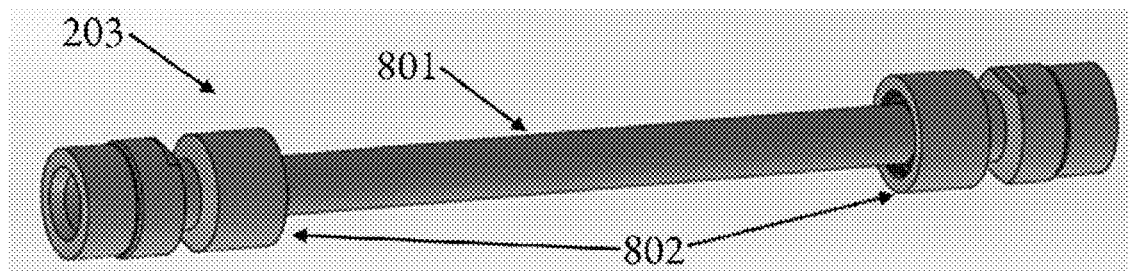
FIG. 8 is one embodiment of the breath cartridge of the disclosed methods, systems, and apparatus, in accordance with an embodiment.
Figure 9:
FIG. 9 is an insert of the embodiment of FIG. 8, in accordance with an embodiment.

In a preferred embodiment, the breath cartridge 203 is not comprised of an absorber, and the VOCs are captured by adsorption onto the walls of one or more channels. Preferably breath cartridge 203 is cooled to a temperature such that when the captured exhaled air equilibrates with the walls of breath cartridge channels 901, the VOC(s) of interest are captured at the desired level. One embodiment of such a breath cartridge 203 is shown in FIG. 8. FIG. 9 shows an insert with multiple linear channels that can be used in the embodiment of breath cartridge 203 presented in FIG. 8. One way to fabricate breath cartridge 203 with multiple channels 901 is to fabricate insert 900 with grooves 901 on its surface, and then press insert 900 into tube 801. The grooves can be of any suitable geometry, for example they might run parallel to the tube, or they might be in the form of multiple spirals along the outside of the insert. Insert 900 can be made of any suitable material. Preferred materials for insert 900 have relatively high thermal conductivity, to minimize heating of the interior walls of channels 901. Preferred materials for insert 900 are metals, preferably aluminum. Preferred materials for tube 801 are metals, preferably stainless steel.

VOCs of interest in exhaled air can range from less than or about 100 parts per billion (PPB), less than or about 10 PPB, less than or about 1 PPB, less than or about 0.1 PPB, and/or less than or about 0.01 PPB. As described above, it is desirable that a large percentage of the VOCs of interest that enter breath cartridge 203 be captured. Preferably the capture efficiency for the VOCs of interest is more than or about 50%, more than or about 90%, more than or about 99%, or more than or about 99.9%. In order to achieve this, the temperature of the breath cartridge 203 should be such that the vapor pressure of the VOCs of interest in equilibrium with the exposed surfaces of the breath cartridge 203 be less than 50%, 10%, 1%, or 0.1% respectively of the partial pressure of the exhaled VOCs of interest. In addition, the dimensions of breath cartridge 203 and the volumetric flow rate of the captured breath must be such that there is sufficient residence time in breath cartridge 203 that a percentage of the VOCs of interest equal to the desired collection efficiency have time to diffuse to the exposed surfaces of the breath cartridge channels 901. The situation is quite analogous to that of water cartridge 202 described above, although more challenging as the diffusion coefficient approximately scales by the inverse square root of molecular weight and the 1.5 power of the temperature, and in general the molecular weights of the VOCs are greater than that of water. Preferably the temperature of breath cartridge 203 is less than or about $-100°$ C., less than or about $-120°$ C., less than or about $-140°$ C., less than or about $-160°$ C., or less than or about $-180°$ C.

In a preferred embodiment, breath cartridge 203 is fully or partially submerged cryogenic fluid 224, preferably in liquid nitrogen 224, and the temperature of the submerged portion of breath cartridge 203 is about $-196$ C. Higher temperatures can be achieved by pressurizing the air above LN2 224, for example using the LN2 boil off and a pressure relief valve, and lower temperatures can be achieved by reducing the pressure, for example using a vacuum pump.

In addition to the temperature requirement, it is also required that the dimensions of breath cartridge 203 and the rate of flow through breath cartridge 203 must be such that the required trapped fraction of the VOC(s) of interest can diffuse to the walls of breath cartridge channels 601 during the residence time of the captured exhaled air in breath cartridge 203. Assuming a temperature dependence of $T^{1.5}$, and a molecular weight dependence of the diffusion coefficient of $m^{-1/2}$, the diffusion coefficient can be estimated for various VOCs by scaling from the diffusion coefficient of a well characterized molecule such as $O_2$, which has a diffusion coefficient at 25° C. of 0.176 $cm^2/s$. The diffusion coefficient of a VOC can be estimated using the following formula: $D=0.176*(T/298.12)^{1.5}*(32/mvoc)^5$ where T is in degrees Kelvin. Knowing the diffusion coefficient, one can calculate the dimensionless diffusion parameter it $\mu=\pi DL/Q$, where L is the length of breath cartridge 203 channel, and Q is the volumetric air flow rate.

With the calculated diffusion parameter, the capture efficiency in percent can be calculated using the following formula adapted from Baron and Willeke (B&W) Aerosol Measurement, 2nd Edition, J Wiley and Sons, 2001:

$$[1-0.81905*e^{-3.6568*\mu}+0.09753*e^{-22.305*\mu}+0325*e^{-56.961*\mu}+0.01544*e^{-107.62*\mu}]*100$$

Because the above expression only depends on $\mu$, one can see that the capture efficiency only depends on D, L, and Q. Because D is proportional to, for a given VOC, $m^{-1/2}$ where m is the molecular weight the capture efficiency can be characterized by $L/(m^{1/2}Q)$. One can calculate that if a capture efficiency greater than 50% is desired, $L/(m^{1/2}Q)>C$, where C=1.5. If a capture efficiency of greater than 75% is desired, C=3.5. If a capture efficiency of greater than 90% is desired, C=6. If a capture efficiency of greater than 95% is desired, C=8. If a capture efficiency of greater than 99% is desired, C=13.

In the same way as for water cartridge 202 as discussed above, it can be shown that the capture efficiency of breath cartridge 203 is independent of the diameter (or equivalent cross-sectional dimension for non-circular cross section channels) of channels 901, and that the length L is the combined length of multiple channels 901.

In one embodiment, it is desired to capture 99% of the undecane ($C_{11}H_{24}$) vapor in exhaled air in breath cartridge 203. The estimated diffusion coefficient of undecane at $-196°$ C. is 0.0105 $cm^2/s$. Using the information above, the desired capture efficiency can be achieved by transporting the captured breath at a flow rate of 0.4 LPM through breath cartridge 203 held at a temperature of $-196°$ C., wherein water cartridge 202 is comprised of 16 channels of length 4.0 cm.

As an alternative to immersion in LN2 224, breath cartridge 203 can be cooled by any means, including but not limited to a standard refrigerator or a Peltier thermoelectric cooler (TEC) (not shown). Preferred TEC embodiments include but are not limited to 4 or more stage, 5 or more stage, 6 or more stage, or 7 or more stage TECs.

FIG. 6 shows the saturated vapor pressures for a non-limiting selection of potentially interesting VOCs (the steep curves) and the corresponding expected vapor pressure of the exhaled VOCs based on literature values (the flatter curves). The point where the curves cross is where the VOCs become saturated in air. As can be seen from the curves, all of these expected exhaled VOC concentrations become saturated at temperatures well above that of LN2, $-196°$ C. For example, isoprene is expected to be saturated when cooled to about $-167°$ C., the lowest temperature of any of the VOCs analyzed on FIG. 6. At a temperature of approximately $-185°$ C., the saturation pressure is three orders of magnitude below the expected pressure of the exhaled isoprene. At $-196°$ C., the collection efficiency of the breath cartridge 203 will generally be limited by the physical dimensions of the breath cartridge 203 channels, and not by the temperature.

Preferably, the total length of channels 901 in breath cartridge 203 (channel 901 length times the number of channels 901) will be greater than or about 20 cm, greater than or about 30 cm, greater than or about 40 cm, greater than or about 50 cm, greater than or about 60 cm, or greater than or about 70 cm.

Figure 10A:
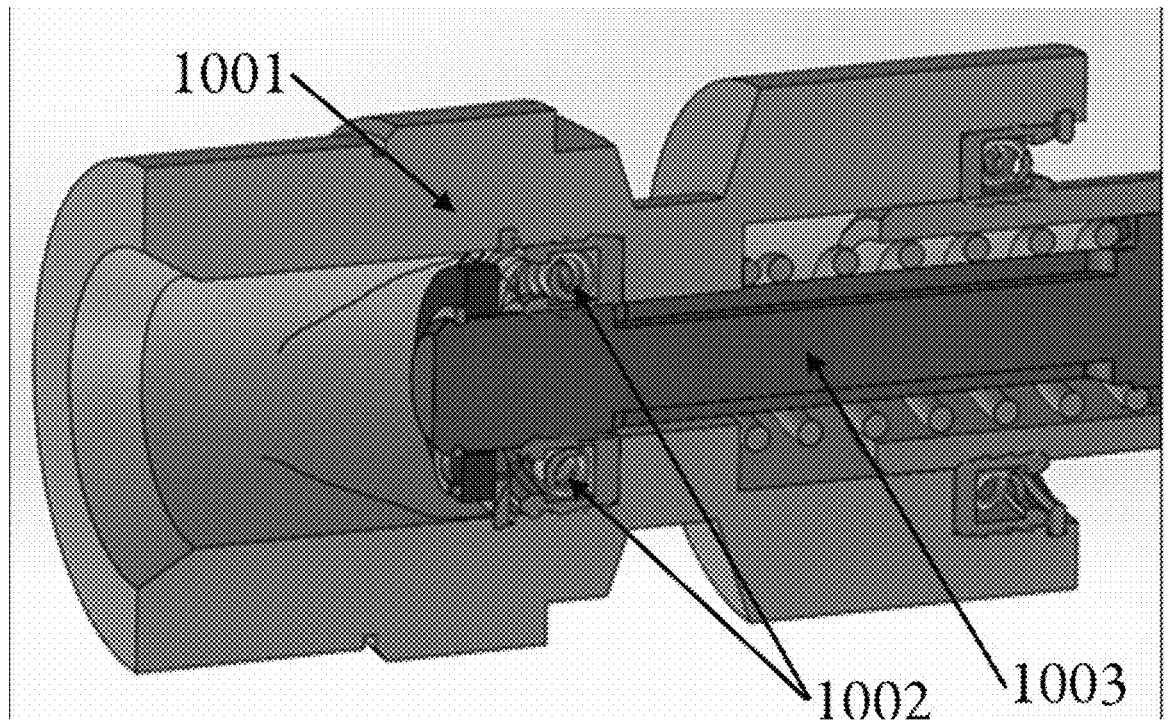
FIGS. 10*a-b* are the VOC valve of the embodiment of FIG. 8, in accordance with an embodiment.
Figure 10B:
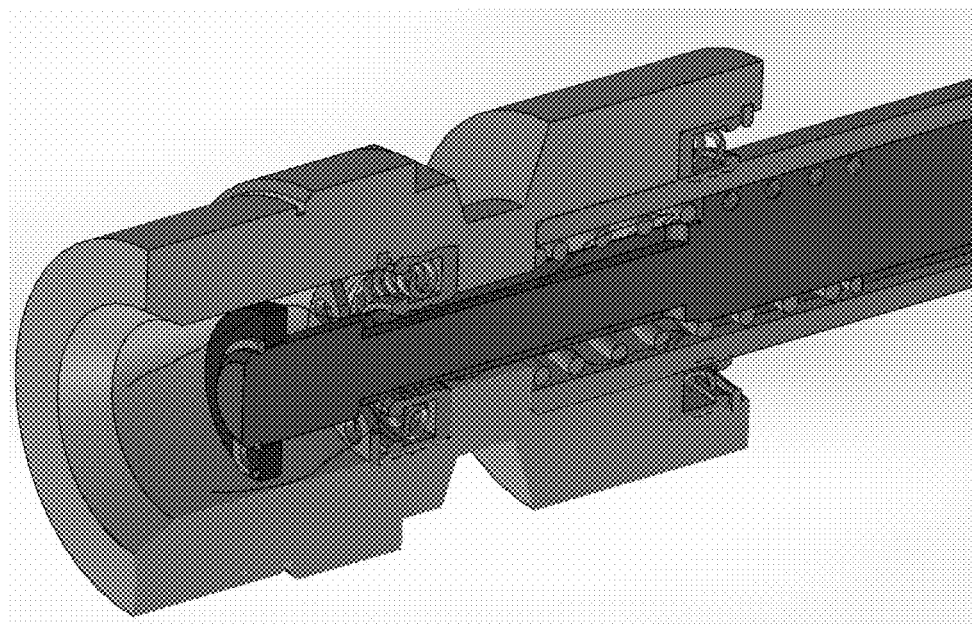

Preferably, breath cartridge 203 may have valves 1001 on each end of breath cartridge 203 that allow breath cartridge 203 to be closed off after trapping the VOCs and kept sealed during storage and transport. FIGS. 10a-b show one embodiment of breath cartridge 203 valves 1001 that are incorporated into end caps 802 of breath cartridge 203 shown in FIG. 8 and utilize insert 900 of FIG. 9. FIG. 10a shows one valve in the closed position. Flow of air may be blocked by seal 1002. FIG. 10b shows valve 1001 in the open position. Valve 1001 is actuated pressing end caps 802 of the breath cartridge 203 of FIG. 8 together. This slides seal 1002 down shaft 1003 of the insert, exposing seal 1002 to axial groove 902 on shaft 1003 of insert 900, allowing captured exhaled air to flow through groove 902 and thereby through breath cartridge 203.

In another embodiment, the breath cartridge 203 is comprised of a length of tubing with valves, preferably ball valves. Preferably the tubing has an outside diameter greater than or about $\frac{1}{16}$", greater than or about $\frac{1}{8}$", greater than or about $\frac{3}{16}$", or greater than or about $\frac{1}{4}$". Preferably, the inside diameter is greater than or about $\frac{1}{5}$ the outside diameter, greater than or about $\frac{1}{4}$ the outside diameter, greater than or about $\frac{1}{2}$ the outside diameter, greater than or about 75% the outside diameter, or greater than our about 90% the outside diameter. The length is selected such that predicted collection efficiency for VOCs of interest (as described earlier) is greater than or about 50%, greater than or about 75%, greater than or about 90%, greater than or about 95%, greater than or about 99%, or greater than or about 99.9%.

The length is preferably increased by an amount of more than or about 4 cm, more than or about 6 cm, more than or about 8 cm, more than our about 10 cm, more than or about 15 cm, or more than or about 20 cm, in order that the valves are kept away from LN2 224 and maintain a temperature within their operating temperature range, preferably −20° C. or greater. Optionally, the valves maybe heated to controlled temperature. Immersion of longer lengths in LN2 224 can be accommodated by using a coiled design. One embodiment of the coil breath cartridge 203 has a length of 100 cm tubing with in inside diameter of 0.05 cm. If 90 cm of the length of the length is immersed in LN2 224, and captured breath is passed through the tube at a flow rate of 0.5 lpm, the predicted capture efficiency of undecane (one of the harder to captures VOCs due its relatively high molecular weight of 156.31) is 99.4%.

Figure 11:
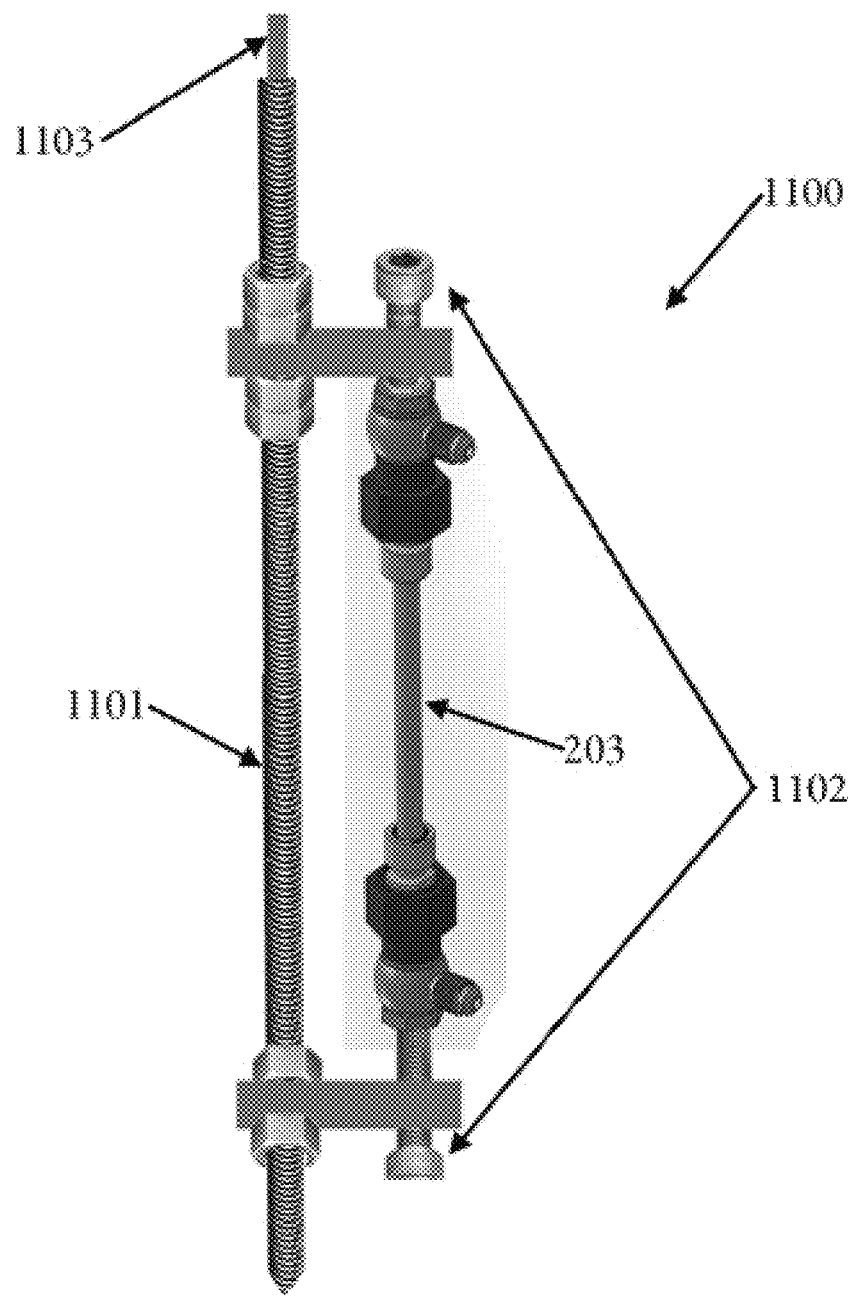
FIG. 11 is an embodiment of the VOC valve actuator that can be used with the breath cartridge of FIG. 8, in accordance with an embodiment.

Preferably, breath cartridge 203 valves 1001 are closed essentially immediately after removal from LN2 224 to ensure that the VOCs do not escape from breath cartridge 203 when the breath cartridge 203 warms up. More preferably, breath cartridge 203 valves 1001 are actuated while breath cartridge 203 is still under LN2. FIG. 11 shows a possible embodiment of breath cartridge 203 valve actuating mechanism 1100. Threaded rod 1101 is used to locate two screws 1102 on either end of breath cartridge 203. Before submerging in LN2 224, upper screw 1102 is advanced to open valves 1001. After trapping of the VOCs, upper screw 1102 is retracted, closing breath cartridge valves 1001. In a preferred embodiment, section 1103 of the top of threaded rod 1101 is turned down to a diameter of a hole in water cartridge 202 and is used as cold finger 225 to cool water cartridge 202.

Preferably the pressure in breath cartridge 203 while it is submerged in LN2 224, for example during trapping of the VOCs, is above or about equal to the ambient air pressure. Preferably the pressure in the breath cartridge 203 is above the pressure in LN2 224 at the lowest point of the breath cartridge 203, so that if there is a leak, LN2 does not enter system 200. At a depth of 6" in LN2 224, the pressure head of LN2 224 is about 1.2 kPa. Preferably the gauge pressure inside breath cartridge 203 is kept at more than or about 0.5 kPa, 1 kPa, 2 kPa, 3 kPa, 5 kPa, 10 kPa, 15 kPa, or 20 kPa.

When valves 1001 on breath cartridge 203 are closed and breath cartridge 203 is warmed up to ambient temperature, the pressure of the gas inside of breath cartridge 203 at 77° K will rise by approximately the ratio of the final temperature (in Kelvin) to the temperature of LN2, 77° K. For the example where the initial pressure is 1 atmosphere (101.3 kPa) plus 2 kPa to keep the pressure above that of LN2 224 (see previous paragraph), 103.3 kPa, and during transport or storage the breath cartridge 203 is exposed to a temperature of 313° K (40° C.), the final pressure in the breath cartridge 203 is 103*313/77=419 kPa or 4.13 atmospheres. In addition, if exhaled CO2 is captured in the breath cartridge 203, upon warming the CO2 will return to the gas phase and contribute to the pressure. Normal air that is exhaled from the lung periphery will have CO2 levels ("end tidal CO2") of about 0.05 atmosphere pressure. By way of example, if breath containing 5% CO2 is captured in breath chamber 204 of volume 100 ml and is subsequently concentrated into a 1 ml breath cartridge 203, the final pressure after warming to room temperature will be 0.05 atm*100 ml/1 ml=5 atm. Thus breath cartridge 203 and breath cartridge valves 1001, depending of the breath cartridge 203 volume, breath chamber volume, and whether CO2 is captured in the breath cartridge 203, should be capable of withstanding an internal pressure of more than or about 4 atmospheres, more than or about 4.5 atmospheres, more than or about 5 atmospheres, more than or about 7.5 atmospheres, more than or about 10 atmospheres, more than or about 20 atmospheres, more than or about 30 atmospheres, or more than or about 40 atmospheres.

Preferably the internal surface area of breath cartridge channel(s) 901 is minimized so that a minimal amount of the VOC(s) is bound to the surface area exposed to the captured breath after breath cartridge 203 is warmed up to room temperature. Preferably the total surface area exposed to the captured breath is less than or about 50 cm$^2$, less than or about 25 cm$^2$, less than or about 15 cm$^2$, less than or about 10 cm$^2$, or less than or about 5 cm$^2$.

In order that a sufficiently high percentage of the VOC(s) are released when valves 1001 are opened for assay, the breath cartridge 203 can be heated prior to opening the breath cartridge valves 1001 for assay. Breath cartridge 203 can be heated to a temperature of greater than or about 50° C., greater than or about 50° C., greater than or about 75° C., greater than or about 100° C., greater than or about 150° C., greater than or about 200° C., or greater than or about 250° C. Preferably the materials of breath cartridge 203 and the surface area of channels 901 are such that no heating is required. Preferably at the release temperature breath cartridge 203 releases more than or about 50% of the captured VOC(s), more than or about 90%, more than or about 95%, or more than or about 99%.

If breath cartridge 203 and some of the tubing leading up to breath cartridge 203 are submerged in LN2 224, it is possible that they will trap about 1% to about 25% of the VOC(s) of interest. Thus it is preferred to have first breath cartridge valve 1001 and all tubing and fittings upstream from it outside of LN2 224, preferably at a temperature above or about −150° C., at or above −125° C., at or above −100° C., or at or above −125° C. As can be seen from FIG. 7, none of the VOCs displayed will reach saturation above −100° C. except undecane, which is slightly above −100° C. Thus it is preferred that the temperature of the first breath cartridge valve 1001 be kept at or above about −100° C. It is important that this does not cause warming of channel(s) 901. This can be accomplished by the design of breath cartridge 203, for example utilizing low thermal conduction components between the first valve 1001 and the breath cartridge channels 901. Preferably the inlet side of the breath cartridge 203, to the first breath cartridge valve 1001, is actively heated, preferably by applying current to power resistor R2 220, and possibly including a temperature control similar to that described for water cartridge 202.

In some configurations, it may be preferable to ensure that ambient air is not in the breath cartridge 203 from the time it is submerged in LN2 224. Air in the breath cartridge 203 can cause ice to form in the breath cartridge 203, potentially blocking or altering the capture characteristics of the breath cartridge 203. Also it has been found that if the tubing connecting to the breath cartridge 203 is open to air on the other end, when immersed in LN2 the breath cartridge 203 can actually pump air into the open end at a rate of order 100 ml/minute, presumably due to condensation of air components such as nitrogen (which is at slightly elevated pressure, see discussion above, and thus will condense at −196° C.) and water in the breath cartridge 203. Thus, as shown in FIG. 2, system 200 is preferably supplied with a source 210 of purge gas preferably inert purge gas. Preferred inert gasses include but are not limited to argon, xenon, nitrogen or krypton, preferably neon, most preferably helium. Hydrogen, although not inert, has a boiling point lower than nitrogen, and thus will not be prone to condensation in the breath cartridge 203 and thus can be used as a purge gas. The purity of the purge gas is preferably higher than or about 99.9%, higher than or about 99.99%, higher than or about 99.999%, or higher than or about 99.9999%. Preferably the amount(s) of VOC(s) of interest in the purge gas in the total volume of purge gas passed through the breath cartridge 203 when the temperature of the breath cartridge 203 is −196° C. are less than or about 10%, less than or about 1%, or less than or about 0.1%, of the amounts expected in the captured volume of exhaled air.

It is preferable that LN2 224 does not leak into breath cartridge 203, because when the breath cartridge 203 warms up, the pressure in breath cartridge 203 will increase until the sealing of breath cartridge 203 is compromised. Therefore, it is preferable that the gauge pressure of the purge gas in breath cartridge 203 be higher than the pressure head of LN2 224 at the depth of the deepest system component in LN2 224. For example, at a depth in LN2 224 of 15 cm, the pressure is about 1.2 kPa above the ambient air. Thus, it is preferable that the purge gas in the breath cartridge 203 be kept at a gauge pressure above 1.2 kPa, at or above 2 kPa, at or above 3 kPa, at or above 5 kPa, or at or above 10 kPa. In addition, it is important to control the flow rate of the captured breath when it flow through breath cartridge 203 because capture efficiency is impacted by flow rate as discussed above. In the embodiment of FIG. 2, pressure and flow rate in breath cartridge 203 are simultaneously controlled by adjusting the pressure of the purge gas using pressure regulator 214 and adjusting the flow restriction using needle valve 216 while monitoring pressure as measured by pressure transducer 218 and flow as measured by flow meter 215.

Ball valve 217 can be used in conjunction ball valves 219 and 207 to isolate breath cartridge 203. This can be a diagnostic for leaks, either by monitoring the pressure decay using pressure transducer 218, or by checking for a large, rapid increase in pressure due to LN2 vaporization while slowly raising breath cartridge 203 out of the LN2 224 bath.

In a non-limiting example, the use of system 200 shown in FIG. 2 is as follows:

1: Attach a clean breath cartridge 203 to system 200.
2: Turn ball valve 208 so that purge gas tank 210 is attached to breath chamber 204 through pressure regulator 214.
3: Turn ball valve 207 so that breath chamber 204 is attached to ball valve 219.
4: Turn ball valve 219 so that breath chamber 204 is attached to the breath cartridge 203 through optional water cartridge 202 and optional CO2 cartridge 213.
5: Open the main valve of purge gas tank 210.
6: Adjust pressure regulator 214 and needle valve 216 such that pressure transducer 218 is at 10 kPa and flow meter 215 reads 0.4 LPM.
7: Purge system 200 by allowing purge gas to flow for 10 minutes.
8: Turn ball valve 219 so it is attached to purge gas tank 210.
9: Verify that the pressure and flow rate are as specified in step 6, adjust as necessary.
10: Place the breath cartridge 203 in cryostat 223.
11: Fill cryostat 223 with LN2 224 by pouring LN2 224 over water cartridge 202.
12: Set temperature of water cartridge temperature controller to −55° C. and allow the temperatures of the breath cartridge 203 and water cartridge 202 to equilibrate.
13: While breath cartridge 203 is equilibrating, verify that the pressure and flow rate remains as specified in step 6, adjust as necessary.
14: Turn ball valve 208 so that breath chamber 204 is connected to needle valve 209.
15: Instruct the subject inhale, hold their breath for 1 second, seal their lips on mouthpiece 201, and start to exhale.
16: When the pressure indicated by pressure transducer 218 shows an increase indicative of the subject trying to exhale, turn ball valve 207 so that mouthpiece 201 is connected to breath chamber 204.
17: When the subject has exhaled 1 liter as measured by integrating the flow rate as measured by the previously calibrated pressure transducer 218, turn ball valve 207 so that breath chamber 204 is connected to ball valve 219.
18: Immediately move ball valve 208 so that it is connected to purge gas tank 210.
19: Instruct the subject to stop exhaling.
20: Turn ball valve 219 so that it is connected to ball valve 207.
21: Verify that the pressure and flow rate are as specified in step 6, adjust as necessary.
22: Allow the purge gas to drive the captured breath from breath chamber 204 through CO2 cartridge 213, water cartridge 202, and breath cartridge 203 for 10 minutes.
23: Close he breath cartridge 203 valves using the breath cartridge valve actuator 1100 (not shown).
24: Remove breath cartridge 203 from LN2 224.
25: Set the set point temperature of water cartridge 202 to 400K.
25: Warm breath cartridge 203 to room temperature using a heat gun.
26: Remove breath cartridge 203 and submit for assay.
27: Allow the purge gas to flow through breath chamber 204 and water cartridge for 10 minutes to remove water and any residual VOCs from system 200.
28: Repeat steps 1-27 as required for the next subject.

The methods, devices, and systems disclosed herein are shown and described in a manner which is considered to be the most practical and preferred embodiments. It is recognized, however, that departures may be made therefrom which are within the scope of the invention and that obvious modifications will occur to one skilled in the art upon reading this disclosure.

While the present disclosure has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A system comprising:
a mouth piece configured to seal to a pair of lips of a subject and receive an exhaled air from the pair of lips of the subject;
a breath chamber configured to receive the exhaled air from the mouth piece;
a valve configured to do one or more of: (a) direct the exhaled air along a desired flow path, (b) direct a purge gas along the desired flow path, (c) control a rate of flow of the purge gas, (d) control a rate of flow of the exhaled air, (e) block a flow of the purge gas, or (f) block a flow of the exhaled air;
a source of the purge gas;
a $CO_2$ cartridge configured to remove $CO_2$ from the exhaled air;
a water cartridge configured to remove water from the exhaled air;
a breath cartridge configured to capture a VOC from the exhaled air, wherein the breath cartridge comprises:
  a single channel with walls to adsorb the VOC;
  a first valve on a first end of the breath cartridge; and
  a second valve on a second end of the breath cartridge, wherein the first and second valves are actuated by translating the first and second valves towards each other;
a temperature control system configured to control a temperature of one or more of: (a) a $CO_2$ cartridge, (b) a water cartridge, or (c) a breath cartridge;
a cryostat configured to contain and limit a heat flow to a cryogenic liquid;
a flow meter designed to measure a flow of one or both of: (a) the exhaled air, or (b) the purge gas; and
a pressure transducer designed to measure one of: (a) a pressure, (b) a flow rate, or (c) a flow volume,
wherein the breath cartridge is at least partially submerged in the cryogenic liquid of the cryostat.

2. The system of claim 1, further comprising a cooling system, wherein the cooling system includes the cryogenic liquid that comprises a liquid nitrogen (LN2).

3. The system of claim 2, wherein the valve is configured to direct the exhaled breath through the breath cartridge when the subject is not exhaling.

4. The system of claim 3, wherein at least 50% of the breath cartridge is submerged in LN2.

5. The system of claim 1, wherein the breath cartridge includes a gauge pressure, and further comprising two or more elements that allow for a simultaneous control of the gauge pressure in the breath cartridge and a flow of the exhaled air through the breath cartridge, wherein the two or more elements are selected from a list consisting of:
  a flow restriction;
  a pressure regulator;
  a flow controller; and
  a needle valve.

6. The system of claim 1, wherein the breath cartridge includes a channel, wherein given a molecular weight m of the VOC, a combined length L of the channel and a total flow rate at a room temperature Q of the exhaled air flowing through the breath cartridge satisfy a relationship:

$$L/(m^{0.5}Q)>C$$

wherein L is in cm, m is in atomic mass units, Q is in liters per minute, and C=1.5.

7. The system of claim 6, wherein C=6.
8. The system of claim 6, wherein C=8.
9. The system of claim 6, wherein C=13.
10. The system of claim 6, wherein the water cartridge is in series with the breath cartridge, wherein the breath cartridge has a combined total channel length of L' and the breath cartridge is run at a temperature T, wherein T, L', and Q satisfy a relationship:

$$L*T^{1.5}/(Q*10000)>C$$

wherein Q is in liters per minute, T is in Kelvin, L is in cm, and C=5.

11. The system of claim 10, wherein C=11.
12. The system of claim 10, wherein C=16.
13. The system of claim 10, wherein C=21.

14. The system of claim 2, wherein the mouth piece and the breath chamber are separated from the breath cartridge and the LN2 when the subject exhales the exhaled air into the mouth piece and the breath chamber receives the exhaled air from the mouth piece, and subsequently the breath chamber is integrated with the breath cartridge and the LN2.

15. The system of claim 1, wherein the single channel of the breath cartridge is a first channel of a plurality of channels with walls to adsorb the VOC.

16. The system of claim 1, wherein actuating the first and second valves opens the first and second valves.

17. The system of claim 16, wherein opening the first and second valves comprises opening a flow path through the single channel of the breath cartridge.

18. The system of claim 17, wherein closing the first and second valves comprises closing a flow path through the single channel of the breath cartridge.

19. The system of claim 18, wherein closing the first and second valves comprises sealing gas or fluid or solids within the breath cartridge.

20. The system of claim 1, wherein the first valve comprises a first seal configured to prevent flow of gas or fluid or solids through the first valve in a closed state, and the second valve comprises a second seal configured to prevent flow of gas or fluid or solids through the second valve in a closed state.

21. The system of claim 1, wherein the breath cartridge further comprises:
  a first breath cartridge end cap comprising the first valve; and
  a second breath cartridge end cap comprising the second valve.

22. The system of claim 21, wherein the first and second valves are actuated by applying a force on the first and second breath cartridge end caps to move the first and second breath cartridge end caps along a longitudinal axis of the breath cartridge.

23. The system of claim 22, wherein the first valve is in a closed state at a first position of the first breath cartridge end cap along the longitudinal axis of the breath cartridge, and the first valve is in an open state at a second position of the first breath cartridge end cap along the longitudinal axis of the breath cartridge.

24. The system of claim 23, wherein the second valve is in a closed state at a first position of the second breath cartridge end cap along the longitudinal axis of the breath cartridge, and the second valve is in an open state at a second position of the second breath cartridge end cap along the longitudinal axis of the breath cartridge.

25. The system of claim 24, wherein each of the second position of the first end cap and the second position of the second end cap is closer to a midpoint of the breath cartridge along the longitudinal axis than the first position of the first end cap and the first position of second end cap.

26. The system of claim 25, wherein the first and second valves are closed by removing the force on the first and second breath cartridge end caps to allow the first and second breath cartridge end caps to translate away from each other along the longitudinal axis of the breath cartridge.

27. The system of claim 1, wherein the breath cartridge is removable from the system.

28. The system of claim 27, wherein the system is configured so that the first and second valves are actuated when the breath cartridge is positioned within the system.

29. The system of claim 28, wherein the system is configured so that the first and second valves are actuated when the breath cartridge is at least partially submerged in the cryogenic liquid of the cryostat.

30. The system of claim 27, wherein the breath cartridge is configured so that the first and second valves close upon removing the breath cartridge from the system.

31. The system of claim 1, further comprising a breath cartridge valve actuating mechanism comprising a threaded rod operably connected to a first screw and a second screw.

32. The system of claim 31, wherein the first screw engages with the first valve, and the second screw engages with the second valve.

33. The system of claim 32, wherein advancing the first screw causes the first and second valves to open.

34. The system of claim 33, wherein retracting the first screw causes the first and second valves to close.

35. The system of claim 31, wherein the threaded rod is connected to the water cartridge and partially submerged in the cryogenic liquid.

36. The system of claim 1, wherein the breath chamber is configured to receive a predetermined volume of the exhaled air.

37. The system of claim 14, further comprising a detachable breath sampling subsystem, wherein the detachable breath sampling subsystem comprises the mouth piece, the breath chamber and the valve.

38. The system of claim 37, wherein the detachable breath sampling subsystem is handheld.

39. The system of claim 38, wherein the detachable breath sampling subsystem is configured to collect the exhaled air after a preselected volume of air is exhaled.

40. The system of claim 1, wherein the temperature control system is configured to control the temperature of the $CO_2$ cartridge.

41. The system of claim 1, wherein the $CO_2$ cartridge, the water cartridge and the breath cartridge are operably connected such that the exhaled air is directed to the $CO_2$ cartridge followed by the water cartridge followed by the breath cartridge.

* * * * *